US010922775B2

(12) United States Patent
Moore et al.

(10) Patent No.: US 10,922,775 B2
(45) Date of Patent: Feb. 16, 2021

(54) SYSTEMS AND METHODS FOR AND DISPLAYING PATIENT DATA

(71) Applicant: AirStrip IP Holdings, LLC, San Antonio, TX (US)

(72) Inventors: Stephen Trey Moore, San Antonio, TX (US); Neil R. McQueen, San Antonio, TX (US)

(73) Assignee: AirStrip IP Holdings, LLC, San Antonio, TX (US)

( * ) Notice: Subject to any disclaimer, the term of this patent is extended or adjusted under 35 U.S.C. 154(b) by 0 days.

(21) Appl. No.: 16/384,351

(22) Filed: Apr. 15, 2019

(65) Prior Publication Data
US 2019/0311450 A1 Oct. 10, 2019

Related U.S. Application Data

(63) Continuation of application No. 14/193,246, filed on Feb. 28, 2014, now Pat. No. 10,262,382.
(Continued)

(51) Int. Cl.
*G06Q 50/22* (2018.01)
*G06Q 10/10* (2012.01)
(Continued)

(52) U.S. Cl.
CPC ............ *G06Q 50/22* (2013.01); *G06Q 10/10* (2013.01); *G16H 40/20* (2018.01); *G16H 15/00* (2018.01)

(58) Field of Classification Search
CPC ..... A61B 5/0452; A61B 5/7435; A61B 5/024; A61B 5/04012; A61B 5/0402;
(Continued)

(56) References Cited

U.S. PATENT DOCUMENTS 4,873,987 A 10/1989 Djordjevic et al.
5,581,275 A 12/1996 Glei
(Continued)

FOREIGN PATENT DOCUMENTS

CN 1250532 4/2000
CN 101310512 11/2008
(Continued)

OTHER PUBLICATIONS

Authorized Officer Blaine R. Copenheaver, International Preliminary Report on Patentability International Application No. PCT/US2014/018987, dated Sep. 11, 2015, 7 pages.
(Continued)

*Primary Examiner* — Joseph D Burgess
(74) *Attorney, Agent, or Firm* — Fish & Richardson P.C.

(57) ABSTRACT

Implementations are directed to providing a user of a mobile device access to patient information and patient physiological data. Actions can include receiving user input, the user input indicating a user command to display a task screen, in response to the user input, processing user-specific data to determine one or more patient icons, each patient icon representing a time-sensitive, patient-associated task, and displaying the task screen on the mobile device, the task screen displaying one or more patient icon groups, each patient icon group including a patient icon of the one or more patient icons.

9 Claims, 11 Drawing Sheets
(4 of 11 Drawing Sheet(s) Filed in Color)

Related U.S. Application Data

(60) Provisional application No. 61/788,233, filed on Mar. 15, 2013.

(51) Int. Cl.
*G16H 40/20* (2018.01)
*G16H 15/00* (2018.01)

(58) Field of Classification Search
CPC ...... A61B 5/7275; G16H 40/63; G16H 10/60; G06F 19/00; G06Q 50/22; G06Q 50/24
See application file for complete search history.

(56) References Cited

U.S. PATENT DOCUMENTS

| | | | |
|---|---|---|---|
| 5,788,646 | A | 8/1998 | Fuchs et al. |
| 6,007,491 | A | 12/1999 | Ling et al. |
| 7,447,643 | B1 | 11/2008 | Olson |
| 7,509,264 | B2 | 3/2009 | Hasan |
| 8,255,238 | B2 | 8/2012 | Powell |
| 8,386,540 | B1 | 2/2013 | McAlister et al. |
| 8,856,729 | B2 | 10/2014 | Moore |
| 9,830,425 | B1 | 11/2017 | Nacey |
| 9,996,667 | B2 | 6/2018 | Moore et al. |
| 10,042,979 | B2 | 8/2018 | Moore et al. |
| 10,068,057 | B2 | 9/2018 | Moore |
| 10,217,527 | B2 | 2/2019 | Moore et al. |
| 10,262,382 | B2 | 4/2019 | Moore et al. |
| 2002/0198473 | A1 | 12/2002 | Kumar et al. |
| 2003/0140044 | A1 | 7/2003 | Mok |
| 2003/0204419 | A1 | 10/2003 | Wilkes et al. |
| 2004/0088317 | A1 | 5/2004 | Fabrick |
| 2004/0102710 | A1 | 5/2004 | Kim |
| 2004/0172307 | A1 | 9/2004 | Gruber |
| 2004/0186746 | A1 | 9/2004 | Angst |
| 2005/0015279 | A1 | 1/2005 | Rucker |
| 2005/0055242 | A1 | 3/2005 | Bello et al. |
| 2005/0149364 | A1 | 7/2005 | Ombrellaro |
| 2005/0159981 | A1 | 7/2005 | Nagaeda et al. |
| 2005/0228250 | A1 | 10/2005 | Bitter |
| 2006/0004605 | A1 | 1/2006 | Donoghue |
| 2006/0149597 | A1 | 7/2006 | Powell et al. |
| 2006/0264769 | A1 | 11/2006 | Satin et al. |
| 2007/0094045 | A1 | 4/2007 | Cobbs |
| 2007/0191721 | A1 | 8/2007 | Parker et al. |
| 2007/0203754 | A1 | 8/2007 | Harrington |
| 2008/0129452 | A1 | 6/2008 | Agrawal et al. |
| 2008/0216060 | A1 | 9/2008 | Vargas |
| 2008/0281168 | A1* | 11/2008 | Gibson ............ A61B 5/0205 600/301 |
| 2009/0054743 | A1 | 2/2009 | Stewart |
| 2009/0216556 | A1 | 8/2009 | Martin |
| 2009/0222286 | A1 | 9/2009 | Elsholz |
| 2009/0248437 | A1 | 10/2009 | Gucciardi |
| 2009/0252516 | A1 | 10/2009 | Otsuka et al. |
| 2010/0125545 | A1 | 5/2010 | Navas |
| 2010/0223071 | A1 | 9/2010 | Kland |
| 2010/0235782 | A1 | 9/2010 | Powell |
| 2010/0328320 | A1 | 12/2010 | Kerstna et al. |
| 2011/0054936 | A1 | 3/2011 | Cowan |
| 2011/0092838 | A1 | 4/2011 | Helfenbein et al. |
| 2011/0138175 | A1 | 6/2011 | Clark et al. |
| 2011/0145012 | A1 | 6/2011 | Nightingale et al. |
| 2011/0172550 | A1 | 7/2011 | Martin et al. |
| 2011/0178814 | A1 | 7/2011 | McGlennen |
| 2011/0191124 | A1 | 8/2011 | Sung |
| 2011/0246235 | A1 | 10/2011 | Powell et al. |
| 2011/0251960 | A1 | 10/2011 | Holla et al. |
| 2011/0275940 | A1 | 11/2011 | Nims |
| 2011/0295078 | A1 | 12/2011 | Reid et al. |
| 2012/0046972 | A1 | 2/2012 | Tonti et al. |
| 2012/0075103 | A1 | 3/2012 | Powell et al. |
| 2012/0131011 | A1 | 5/2012 | Vdovjak et al. |
| 2012/0173257 | A1 | 7/2012 | Preiss |
| 2012/0226771 | A1 | 9/2012 | Harrington |
| 2012/0296672 | A1 | 11/2012 | Bates |
| 2013/0085771 | A1 | 4/2013 | Ghanbari |
| 2013/0086201 | A1 | 4/2013 | Legge |
| 2013/0096649 | A1 | 4/2013 | Martin et al. |
| 2013/0166317 | A1 | 6/2013 | Beardall et al. |
| 2013/0197679 | A1 | 8/2013 | Balakrishnan |
| 2013/0253339 | A1 | 9/2013 | Reyes |
| 2013/0304499 | A1 | 11/2013 | Rangadass |
| 2013/0304512 | A1 | 11/2013 | Seshadri et al. |
| 2014/0006058 | A1 | 1/2014 | Schoenberg |
| 2014/0032242 | A1 | 1/2014 | LaBorde |
| 2014/0095207 | A1 | 4/2014 | Dhir |
| 2014/0122119 | A1 | 5/2014 | Hardy |
| 2014/0249854 | A1 | 9/2014 | Moore et al. |
| 2014/0249855 | A1 | 9/2014 | Moore |
| 2014/0249856 | A1 | 9/2014 | Moore |
| 2014/0249857 | A1 | 9/2014 | Moore et al. |
| 2014/0249858 | A1 | 9/2014 | Moore et al. |
| 2014/0278486 | A1 | 9/2014 | Moore et al. |
| 2014/0278487 | A1 | 9/2014 | Moore et al. |
| 2014/0278488 | A1 | 9/2014 | Moore |
| 2014/0348054 | A1 | 11/2014 | Gaines et al. |
| 2015/0070187 | A1 | 3/2015 | Wiesner et al. |
| 2015/0088549 | A1 | 3/2015 | Moore et al. |
| 2015/0254412 | A1 | 9/2015 | Humphrys et al. |
| 2015/0371176 | A1 | 12/2015 | Barrett |
| 2017/0053086 | A1 | 2/2017 | Martin et al. |
| 2017/0173262 | A1 | 6/2017 | Veltz |
| 2018/0277255 | A1 | 9/2018 | Martin et al. |
| 2020/0206517 | A1 | 7/2020 | Martin et al. |

FOREIGN PATENT DOCUMENTS

| | | |
|---|---|---|
| WO | WO 2013158625 | 10/2013 |
| WO | WO 2013158632 | 10/2013 |
| WO | WO 2014134293 | 9/2014 |

OTHER PUBLICATIONS

Authorized Officer Blaine R. Copenheaver, International Search Report and Written Opinion for International Application No. PCT/US2014/018987, dated May 22, 2014, 8 pages.

Director General F. A. Dos Santos, African Examination Report for Patent Application No. AP/P/2015/008727, dated Sep. 15, 2017, 4 pages.

Director General F. A. Dos Santos, Second Examination Report and Search Report for African Regional Intellectual Property Organization (ARIPO) Application No. AP/P/2015/008727, dated Jul. 19, 2018, 4 pages.

Examination Report No. 1 for Australian Application No. 2014223470, dated Jan. 10, 2019, 6 pages.

European Examination Report for Application No. 14756271.4, dated Aug. 23, 2016, 4 pages.

European Search Report for Application No. 14756271.4, dated Aug. 8, 2016, 4 pages.

First Office Action for Chinese Application No. 201480024921.X, dated Jul. 18, 2018, 27 pages.

Google patents search, Jan. 9, 2017, 2 pages.

Martinez, I., Escayola, J., Martinez-Espronceda, M., Munoz, P., Trigo, J. D., Munoz, A., Garcia, J.(2010). Seamless integration of ISO/IEEE11073 personal health devices and ISO/EN13606 electronic health records into an end-to-end interoperable solution. Telemedicine and e-Health, 16(10), 993(12). (Year: 2010).

Airstriptech. Airstrip Cardiology iPad Demo. May 2011. [retrieved on Jun. 24, 2013]. Retrieved from the Internet: <URL:http://www.youtube.com/watch?v=6V15m9A4wd0>. Entire document.

Director General F. A. Dos Santos, Third Examination Report for Patent Appln. No. AP/P/2015/008727, dated Jul. 18, 2019, 4 pages.

Examination Report No. 2 for Australian Application No. 2014223470, dated May 10, 2019, 3 pages.

Examination Report No. 3 for Australian Appln. No. 2014223470, dated Aug. 29, 2019, 4 pages.

PRWEb. Cardio Caipers Software from Iconico Released; the On-Screen Electrocardiogram (EKG, ECG) Measurement Software for Windows. PRWeb. Mar. 21, 2006. [Retrieved on: Aug. 13,

(56) References Cited

OTHER PUBLICATIONS

2013]. Retrieved from internet: <URL:http://www.prwed.com/pdfdownload/361236.pdf>.entire document.
CN Office Action in Chinese Appln. No. 201480024921.X, dated Apr. 10, 2020, 10 pages (with English translation).
Director General F.A. Dos Santos, Notification of Decision to Grant for Patent Appln. No. AP/P/2015/008727, dated Sep. 17, 2019, 5 pages.
IN Office Action in Indian Application No. 8906/DELNP/2015, dated Jul. 13, 2020, 9 pages.
Light et al. "Mobile middleware service architecture for EMS application," 2006 1st International Conference on Communication Systems Software & Middleware, 2006, pp. 1-5.
Lomotey et al., "SOPHRA: A Mobile Web Services Hosting Infrastrucutre in mHealth," 2012 IEEE First International Conference on Mobile Services, 2012, pp. 88-95.

* cited by examiner

SYSTEMS AND METHODS FOR AND DISPLAYING PATIENT DATA

CROSS-REFERENCE TO RELATED APPLICATIONS

This application is a continuation of U.S. patent application Ser. No. 14/193,246 filed on Feb. 28, 2014, which claims the benefit of and priority to U.S. Provisional Application No. 61/788,233 filed on Mar. 15, 2013, the disclosure of which are expressly incorporated herein by reference in their entirety.

BACKGROUND

Patient information can be stored across multiple facilities associated with respective health care providers. For example, healthcare continua can include hospitals, clinics, laboratories, and/or other healthcare facilities. In some instances, each healthcare facility had its own data source for storing patient information and data associated with services provided at the respective facility. For example, multiple, different electronic medical records (EMRs) can be provided for a particular patient across a healthcare continuum. In some examples, such EMRs are vendor-specific, storing data and information is disparate formats.

Physicians and other healthcare providers may be required to access patient data and information from across a healthcare continuum. The disparate nature, in which data and information may be stored, can complicate retrieval and display of relevant patient information to healthcare providers.

SUMMARY

Implementations of the present disclosure provide methods for providing a user of a mobile device access to patient information and patient physiological data. In some examples, methods include actions of receiving user input, the user input indicating a user command to display a task screen, in response to the user input, processing user-specific data to determine one or more patient icons, each patient icon representing a time-sensitive, patient-associated task, and displaying the task screen on the mobile device, the task screen displaying one or more patient icon groups, each patient icon group including a patient icon of the one or more patient icons. Other implementations of this aspect include corresponding systems, apparatus, and computer programs, configured to perform the actions of the methods, encoded on computer storage devices.

These and other implementations can each optionally include one or more of the following features: the time-sensitive, patient-associated task of each patient icon includes a pending task; actions further include, in response to user selection of a patient icon, displaying a task-specific screen, the task-specific screen including patient data and/or patient information associated with an underlying task; actions further include receiving user input indicating completion of the time-sensitive, patient-associated task of a patient icon, and in response, providing a signal to a back-end system indicating completion of the time-sensitive, patient-associated task; actions further include removing the patient icon from display in the task screen; actions further include each time-sensitive, patient-associated task is determined to be within a threshold time period; and a time-sensitive, patient-associated task is determined to be within the threshold time period when a difference between a current time and a time associated with the task is within the threshold time period.

Other aspects of the present disclosure provide systems including one or more processors, and a computer-readable medium coupled to the one or more processors having instructions stored thereon which, when executed by the one or more processors, cause the one or more processors to perform one or more of the methods provided herein.

It is appreciated that methods in accordance with the present disclosure can include any combination of the aspects and features described herein. That is to say that methods in accordance with the present disclosure are not limited to the combinations of aspects and features specifically described herein, but also include any combination of the aspects and features provided.

The details of one or more implementations are set forth in the accompanying drawings and the description below. Other features, objects, and advantages will be apparent from the description and drawings, and from the claims.

DESCRIPTION OF DRAWINGS

The patent or application file contains at least one drawing executed in color. Copies of this patent or patent application publication with color drawing(s) will be provided by the Office upon request and payment of the necessary fee.

Like reference symbols in the various drawings indicate like elements.

DETAILED DESCRIPTION

Implementations of the present disclosure are generally directed to an enterprise scalable, data- and vendor-agnostic mobility architecture to securely deliver patient data and information from medical devices, electronic medical records (EMRs) and patient monitors to healthcare providers anywhere across a healthcare continuum. More particularly, implementations of the present disclosure provide integrated and unified views of patient data and patient information on mobile devices (e.g., smartphones, tablets) from a plurality of data sources across the healthcare continuum. As discussed in further detail herein, implementations of the present disclosure enable timely and collaborative clinical decision-making, and enable healthcare systems to better track quality metrics, empower a mobile workforce, expand networks, and achieve clinical transformation.

Example systems and methods that can be included in implementations of the present disclosure are provided in U.S. Provisional Application Ser. No. 61/771,591, filed Mar. 1, 2013, the contents of which are expressly incorporated herein by reference in the entirety.

Figure 1:
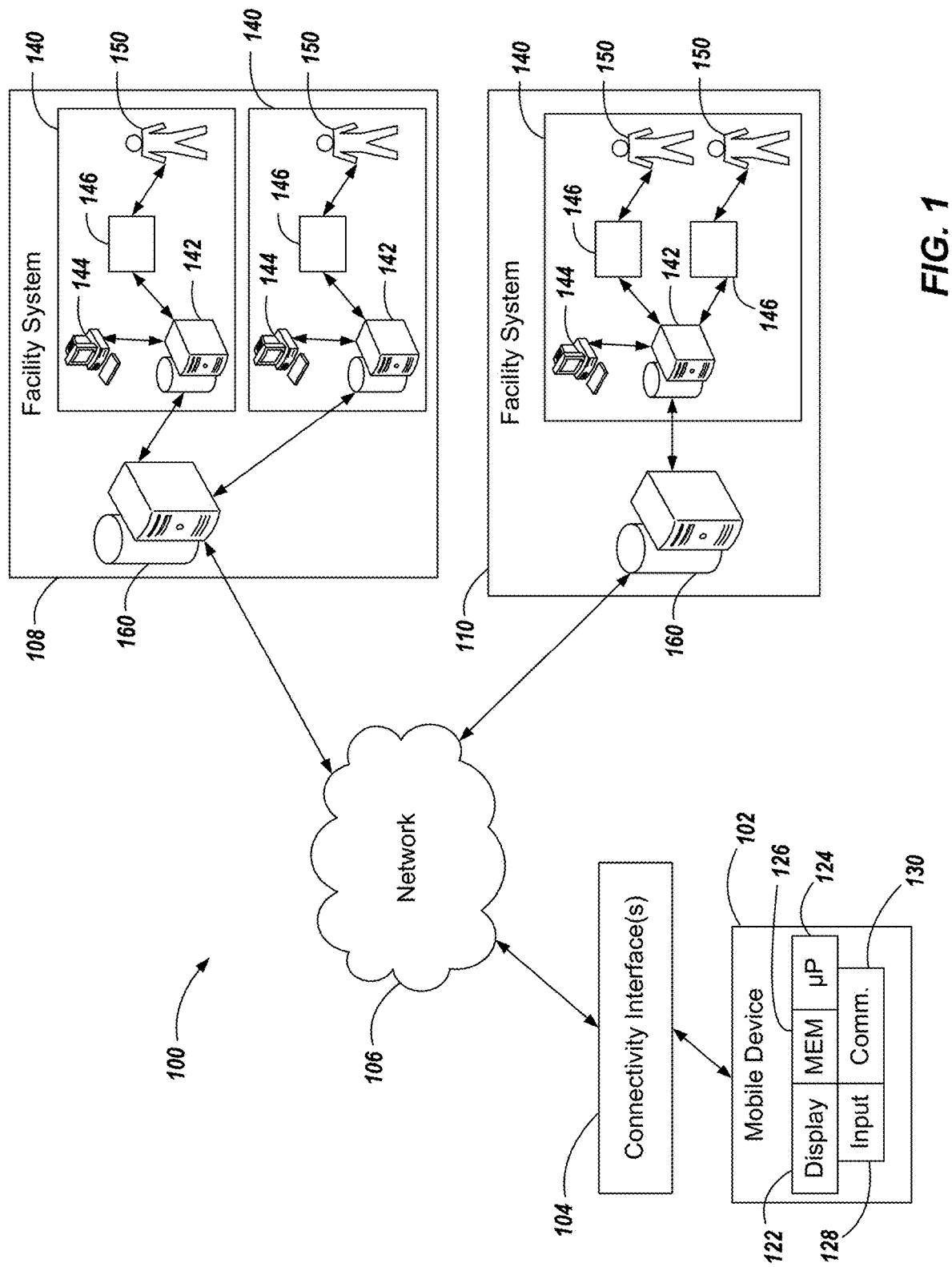
FIG. 1 is a schematic illustration of an example system architecture in accordance with implementations of the present disclosure.

Referring now to FIG. 1, an example system architecture 100 is illustrated, and includes a mobile device 102, connectivity interface(s) 104, a network 106, a first facility system 108, and a second facility system 110. As discussed in further detail herein, data is transferred from each of the first and second facility systems 108, 110 through the network 106 and connectivity interface(s) 104 for presentation, or display on the mobile device 102. Further, data can be transferred from the mobile device 102 through the connectivity interface(s) 104 and the network 106 to each of the first and second facility systems 108, 110. Although a single mobile device 102 is illustrated, it is contemplated that one or more mobile devices 102 can communicate with each of the first and second facility systems 108, 110 through the network 106 and the connectivity interface(s) 104. Similarly, although two facility systems are illustrated, implementations of the present disclosure can include one or more facility systems.

The mobile device 102 can include any number of example devices. Such example devices include, but are not limited to, a mobile phone, a smartphone, a tablet computing device, a personal digital assistant (PDA), a laptop personal computer (PC), a desktop PC, and/or appropriate combinations thereof. In the depicted example, the mobile device 102 includes a display 122, a processor 124, memory 126, an input interface 128, and a communication interface 130. The processor 124 can process instructions for execution of implementations of the present disclosure. The instructions can include, but are not limited to, instructions stored in the memory 126 to display graphical information on the display 122. Example displays include, but are not limited to, a thin-film-transistor (TFT) liquid crystal display (LCD), or an organic light emitting diode (OLED) display. The memory 126 stores information within the mobile device 102. In some implementations, the memory 126 can include a volatile memory unit or units, and/or a non-volatile memory unit or units. In other implementations, removable memory can be provided, and can include, but is not limited to, a memory card. Example memory cards can include, but are not limited to, a secure digital (SD) memory card, a mini-SD memory card, a USB stick, and the like.

In some examples, the input interface 128 can include a keyboard, a touchscreen, a mouse, a trackball, a microphone, a touchpad, and/or appropriate combinations thereof. In some implementations, an audio codec (not shown) can be provided, which receives audible input from a user or other source through a microphone, and converts the audible input to usable digital information. The audio codec can generate audible sound, such as through a speaker that is provided with the mobile device 102. Example sounds can include sound from voice telephone calls, recorded sound (e.g., voice messages, music files, etc.), and/or sound generated by applications operating on the mobile device 102.

The mobile device 102 may communicate wirelessly through the communication interface(s) 104, which can include digital signal processing circuitry. The communication interface(s) 104 may provide communications under various modes or protocols including, but not limited to, GSM voice calls, SMS, EMS or MMS messaging, CDMA, TDMA, PDC, WCDMA, CDMA2000, and/or GPRS. Such communication may occur, for example, through a radio-frequency transceiver (not shown). Further, the mobile device can be capable of short-range communication using features including, but not limited to, Bluetooth and/or WiFi transceivers (not shown).

The mobile device 102 communicates with the network 106 through the connectivity interface(s) 104. In some examples, the connectivity interface(s) 104 can include a satellite receiver, cellular network, a Bluetooth system, a Wi-Fi system (e.g., 802.x), a cable modem, a DSL/dial-up interface, a private branch exchange (PBX) system, and/or appropriate combinations thereof. Each of these connectivity interfaces 104 enables data to be transmitted to/from the network 106. In some examples, the network 106 can be provided as a local area network (LAN), a wide area network (WAN), a wireless LAN (WLAN), a metropolitan area network (MAN), a personal area network (PAN), the Internet, and/or combinations thereof.

Figure 2:
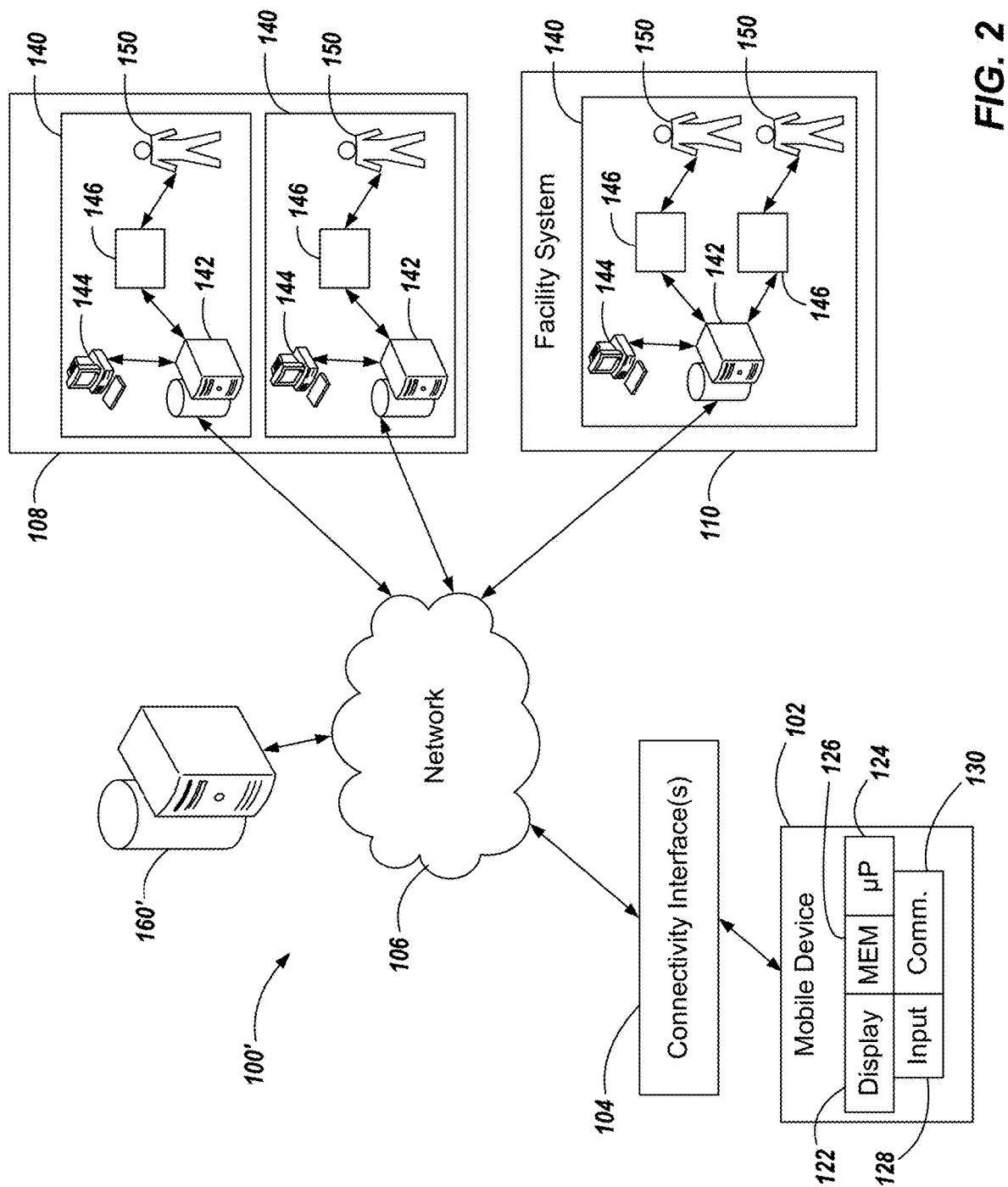
FIG. 2 is a schematic illustration of another example system architecture in accordance with implementations of the present disclosure.

In the example systems of FIGS. 1 and 2, the first facility system 108 includes a plurality of facilities 140, and the second facility system 110 includes a facility 140. It is contemplated that each facility system 108, 110 can include one or more facilities, and is not limited to the example arrangement described herein. In the case of multiple facilities, the facilities can be remotely located from one another, and/or can be located at a common location, or site (e.g., separate departments in a common (the same) building). Each facility system 108, 110 can be provided as a medical care system, for example, which medical care system can include one or more hospitals, hospital systems, clinics, physician offices, and the like.

In some examples, each facility 140 includes an associated information system 142, computer interface(s) 144, and patient monitoring device(s) 146. Example information systems can include, but are not limited to, a clinical information system (CIS), an EMR system, an electronic health record (EHR) system, and/or a hospital information system (HIS). Each information system 142 can be provided as a server, and supports the acquisition, storage, modification, and distribution of clinical information, such as patient data, throughout the facility 140 and/or facility system 108, 110. In some examples, each information system 142 can communicate with one or more ancillary information systems (not shown) that can include, but are not limited to, a pharmacy management system, a laboratory management system, and/or a radiology management system. Although the example system architecture 100 includes an information system 142 located at each facility 140, it is contemplated that the facilities 140 can communicate with a common information system 142 that is remotely located from either facility 140, or that is located at one of the facilities 140 within the facility system 108, 110.

In some examples, the computer interface 144 can communicate with the information system 142 to enable access to information that is stored within, and managed by the information system 142. In some examples, the computer interface 144 can include a personal computer (PC) (e.g., desktop, laptop, or tablet). Although a single computer interface 144 is illustrated in the example architectures described herein, it is contemplated that one or more computer interfaces 144 can communicate with the information system 142. Communication between each computer interface 144 and the information system 142 can be achieved via a direct connection, or remotely through a network (not shown) that can include, but is not limited to, a LAN, a WAN, a WLAN, and/or the Internet.

In some examples, each patient monitoring device 146 monitors physiological characteristics of a particular patient 150, and generates data signals based thereon. As discussed in further detail herein, implementations of the present disclosure provide patient monitoring devices that include a computing device, such as a tablet computing device. The data signals are communicated to the information system 142, which collects patient data based thereon, and stores the data to a patient record that is associated with the particular patient. An example patient record can include an electronic medical record (EMR). Although a single patient monitoring device 146 is illustrated per each patient 150, it is contemplated that multiple patient monitoring devices 146 can monitor a particular patient 150. The patient monitoring device(s) 146 can communicate with the information system 142 via a direct connection, or remotely through a network (not shown) that can include, for example, a LAN, a WAN, a WLAN, and/or the Internet.

In some examples, the patient data is made available for display on the computer device 144. A healthcare provider (e.g., a nurse and/or physician) can augment the patient data by inputting patient information that is also stored to the information system 144. More specifically, the healthcare provider can input patient information corresponding to a particular patient 150, which patient information can be stored to the patient record (e.g., EMR). As one example, a nurse can input nursing notes, which nursing notes can be stored to the patient record in the information system. Example patient information can include any non-physiological information corresponding to a patient (e.g., name, age, date-of-birth (DOB), gender).

As discussed above, each information system 142 stores patient data that can be collected from the patient monitoring devices 146, as well as additional patient information, that can include information that is input by a healthcare provider. The information system 144 communicates the patient data and/or the additional patient data to a data management system (DMS) 160. The DMS 160 can be provided as a server, or a virtual server, that runs server software components, and can include data storage including, for example, a database and/or flat files. In the example system architecture 100 of FIG. 1, each facility system 108, 110 includes a corresponding DMS 160. In such an arrangement, each information system 142 communicates patient data, and/or additional patient data to the DMS 160. Furthermore, and as discussed in further detail below, the DMS 160 can communicate ancillary information to the information system 142. Communication between the DMS 160 and the information system(s) 142 can be achieved via a direct connection, or remotely through a network (not shown) that can include, for example, a LAN, a WAN, a WLAN, and/or the Internet.

In some examples, a DMS 160 corresponding to a particular facility system can be remotely located from any of the facilities 140 of the facility system 108, 110, or can be located at a particular facility 140 of the facility system 108, 110. In the example system architecture 100 of FIG. 1, the DMS 160 is remotely located from either facility 140 within each of the facility systems 108, 110. It is contemplated, however, that the DMS 160 can be located at one of the facilities 140, and remote from the other facility 140.

In the example system architecture 100' of FIG. 2, a DMS 160' is provided that is common to (the same for) the facility systems 108, 110. For example, the DMS 160' can be described as being common to various facility systems 108, 110, and is not associated with a particular facility system 108, 110. For example, the DMS 160' can be hosted by a third-party vendor (e.g., a cloud service provider). In some examples, each information system 42 communicates with the DMS 160' via a direct connection, or remotely through a network (not shown) that can include, but is not limited to, a LAN, a WAN, a WLAN, and/or the Internet. In the example arrangement of FIG. 2, the DMS 160' communicates with each of the information systems 142 through the network 106. The information systems 142 communicate patient data and/or patient information to the DMS 160', and the DMS 160' can communicate ancillary information to the information system 142, as discussed in further detail below.

In the example system architecture 100 of FIG. 1, the facility 140, or facility system 108, 110 installs the DMS 160 as a local DMS, and the DMS 160 sits at the local site with other servers that can include, for example, the information system 142. In some implementations, the DMS 160 can be sectioned off, or separated from a logical network perspective, but still physically exists with the other servers that belong to the respective facility 140. In some examples, server components are installed on the DMS 160, which components can include, for example, a database component, a database synchronization component, a web services component, and/or a structured query language (SQL) component. An information system interface can also be installed on the DMS 160, and functions as the interface to the information system 142. As one example, the information system interface can include OBLink, provided by GE Healthcare. In some implementations, the DMS 160 can be arranged in a multiple server configuration, in which one server only hosts web service related components and is logically segregated, and another server has the remaining necessary server components installed.

The example system architecture 100' of FIG. 2, provides for the remote location of data collection at the DMS 160'. In such implementations, the DMS 160' can be provided at a third-party site, remote from any of the facilities 140, or facility systems 108, 110. The third-party functions as a DMS host, and the necessary server components are installed on the remotely hosted DMS 160'. In some implementations, a business-to-business (B2B) virtual private network (VPN) can be created between the remotely hosted DMS 160' and the network of the facility 140 or facility system 108, 110. In this manner, the facility 140 and/or facility system 108, 110 forgoes the purchase and/or maintenance of another physical server, or DMS 160. Further, the up-time and the status of availability of the DMS 160' are easier to manage on the part of a dedicated third-party. The DMS' access to the network can be attended to by the third-party, as opposed to burdening the facility 140, or the facility systems 108, 110. Further, the third-party can implement virtual server technologies to leverage multiple DMS installations on a single physical server. In such implementations, a plurality of virtual servers are logically partitioned in a single physical server, and each virtual server has the capability of running its own operating system and server components, and can be independently booted.

In accordance with implementations of the present disclosure, the DMS 160, 160' synchronizes and transfers data between the mobile device 102, or multiple mobile devices 102, and the information system 142, or multiple information systems 142. More specifically, the DMS 160, 160' processes and prepares the patient data and/or patient information for transfer to and presentation on the mobile device 102, or multiple mobile devices 102, from the information system 142, and/or other systems, as discussed in further detail herein. The DMS 160, 160' also processes and prepares ancillary information for transfer to and storage in the information system 142 from the mobile device 102, or multiple mobile devices 102 for potential presentation at a corresponding computer device 144. Example DMSs can include, but are not limited to, the AirStrip Server provided by AirStrip Technologies, LLC, which AirStrip Server includes AirStrip Server Components installed therein.

Figure 3:
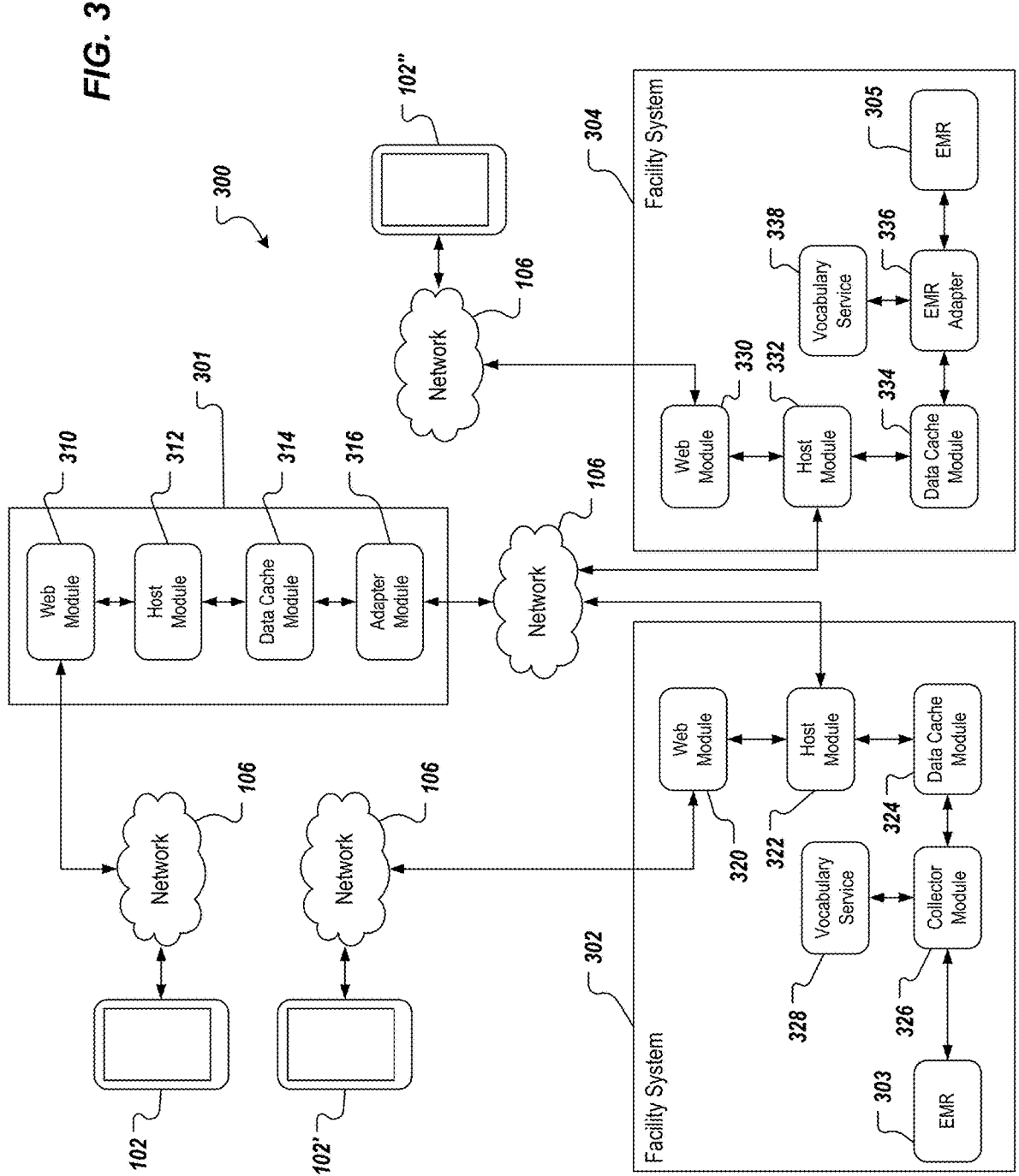
FIG. 3 is a functional block diagram of an example system in accordance with implementations of the present disclosure.
Figure 4:
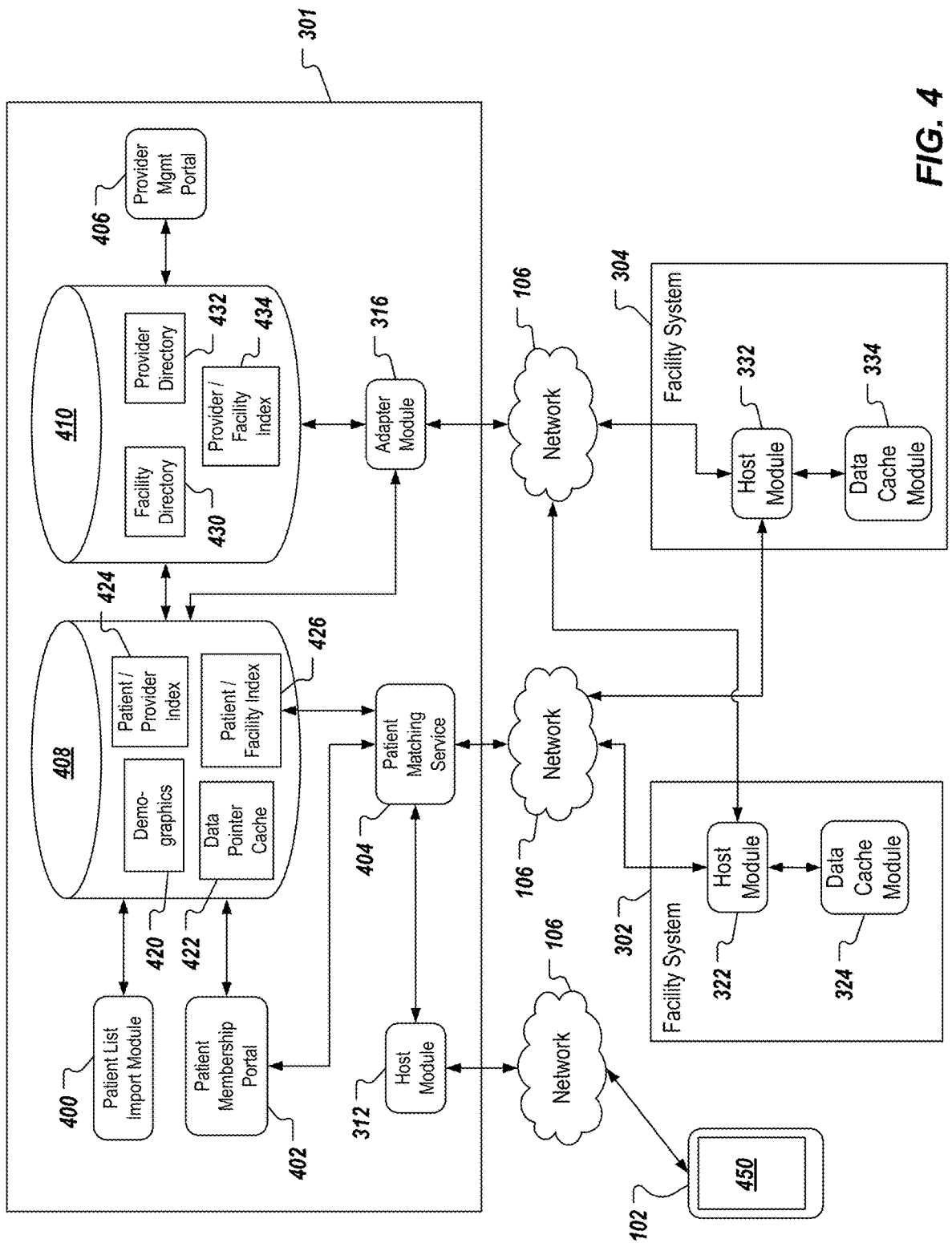
FIG. 4 is a more detailed view of the functional block diagram of FIG. 3.

Referring now to FIGS. 3 and 4, example module structure, or system 300 that can be implemented to provide features of the present disclosure will be described in detail. In some examples, the example system 300 enables patient data and patient information to be communicated to/from, and to be exchanged between mobile devices and data sources across healthcare continua. In some examples, each module can be provided as one or more computer-executable programs that are executed using one or more computing devices (e.g., computing devices provided as part of a DMS, computing devices located at one or more facilities of a facility system).

FIG. 3 illustrates an overview of the example system 300. In the depicted example, the module structure includes modules located at a DMS 301, a first facility system 302 and a second facility system 304. In some examples, the first facility system 302 and the second facility 304 can be included in at least a portion of a healthcare continuum, discussed in further detail herein. The facility system 302 includes a patient record module 303 (e.g., EMR module) that accesses one or more patient records managed and stored by the facility system 302. The facility system 304 includes a patient record module 305 (e.g., EMR module) that accesses one or more patient records managed and stored by the facility system 304.

In the depicted example, and as discussed in further detail herein, patient data and/or information can be provided for integrated and unified display on the mobile device 102 through the network 106 and the DMS 301 from across healthcare continua (e.g., the facility systems 302, 304). In some examples, patient data and/or information can be provided for display on a mobile device 102', 102" through the network 106 from a facility system (e.g., the facility system 302, 304). In some examples, the mobile devices 102, 102', 102" are the same device. That is, for example, a mobile device can receive patient data and/or information from across a healthcare continuum, and/or from individual facility systems.

In some implementations, the DMS 301 includes a web module 310, a host module 312, a data cache module 314 and an adapter module 316, web module 320, a host module 322, a data cache module 324, a collector module 326. In general, modules of the DMS 301 enable the DMS 301 to retrieve and combine data from multiple facility systems (e.g., the facility systems 302, 304) across healthcare continua. In some examples, the web module 310 provides a first-level network facing interface to the DMS infrastructure. In some examples, and in response to a request from a mobile device (e.g., the mobile device 102), the web module 310 performs request validation and user authentication and routes the request to the host module 312. In some examples, the web module 310 includes one or more sub-modules. Example sub-modules include a request validation sub-module, which validates received requests, a user authentication module, which authenticates an identity of the user and/or mobile device from which a request is received, and a request routing sub-module, which routes requests after validation and authentication.

In some implementations, the host module 312 orchestrates request processing. In some examples, the host module 312 includes one or more sub-modules. Example sub-modules include a request parsing sub-module that parses received requests, a pipeline assembly sub-module, a pipeline processing sub-module, an operation execution sub-module, a data access sub-module, a results formatting sub-module, an access control sub-module, an encryption sub-module, a data conditioning sub-module, and a logging sub-module. In some examples, the host module 312 parsers a received request (e.g., using the request parsing sub-module) to determine, for example, what type of device issued the request, which application executing on the device issued the request, and/or patient data/information (or other data such as analytical data, discussed below) is needed to fulfill the request. In some examples, and based on the parsed information, the host module 312 builds a pipeline (e.g., using the pipeline assembly sub-module). In some examples, a pipeline can be provided as a list of tasks that need to be executed to fulfill the request. Example tasks can include retrieving particular patient data/information, processing retrieved patient data to generate additional data and/or data visualizations (e.g., analytical data, trend graphs, discussed below), encrypting/decrypting retrieved data, performing access control to retrieve data, generating logs of tasks.

In some implementations, the host module 312 coordinates data retrieval with the data cache module 314 (e.g., using the data access sub-module). The retrieved data is provided back to the host module 312. In some examples, the host module 312 processes the retrieved data (e.g., using the operation execution sub-module, the results formatting sub-module and/or the data conditioning sub-module). In some examples, the retrieved data is processed to generate additional data (e.g., data used for data visualizations). In some examples, the retrieved data and/or the additional data are conditioned to provide efficient transfer back to the requesting mobile device. In some examples, conditioning can include converting data based on transmission protocol, formatting data for optimal display on the particular device, and/or packaging data to send to the requesting device.

In some implementations, the data cache module 314 enables access to and optional storage of detailed patient data/information used by other components of the system 300. In some examples, the data cache module 314 includes one or more sub-modules and/or data stores. An example sub-module can include a cache services sub-module. In some examples, the data cache module 314 can operate in a pass-through mode (real-time mode) and a reposed mode. In some examples, patient data/information required to satisfy a given request can be directly accessed from a source system (e.g., the facility system 302, 304) in real-time. In such examples, the data cache module 314 operates in a pass-through mode, retrieving the patient data/information from multiple data sources and passing the patient data/information onward for responding to the request. In some examples, an application program interface (API), or other programmatic mechanism can be used to retrieve the patient data/information. In some examples, in the pass-through mode, patient data/information is not stored in a persistent data store accessed by the data cache module 314. In some implementations, it might be desired to improve retrieval performance. Consequently, the data cache module 314 can store data identifiers and/or pointers in a persistent data store. When in the pass-through mode, the data cache module 314 uses the adapter module 316 to perform the actual retrieval of patient data/information from one or more facility systems.

In some examples, the patient data/information that is required to satisfy a request cannot be directly accessed from the facility systems (e.g., the facility systems 302, 304). In such examples, the data cache module 314 operates in the reposed mode. In some examples, in the reposed mode, the data cache module 314 stores a detailed copy of the patient data/information in the persistent data store. That is, for example, stored patient data/information is stored at the DMS-level, but had been retrieved from remote data sources (e.g., data sources located at the facility systems 302, 304). In some examples, when a request is made for patient data/information in the reposed mode, the patient data/information is retrieved directly from the persistent data store (e.g., by the cache services sub-module).

In some implementations, the adapter module 316 enables the retrieval of patient data/information from across healthcare continua. Consequently, the adapter module 316 can be referred to as a federated adapter module. In some examples, in response to receiving a request from the mobile device 102 for patient data/information from multiple data sources (e.g., the facility systems 302, 304), the data cache module 314 utilizes the adapter module 316 to retrieve the requested patient data/information from the multiple data sources. In some examples, the adapter module 316 communicates with local host modules (discussed in further detail below) of the respective facility systems.

In some implementations, the request processing operation of the DMS 301 is stateless. More particularly, the modules of the DMS 301 handle each received request as a distinct unit and, once a request is handled, stores no state information associated with a completed request. In other words, after the DMS 301 has processed a request, the DMS 301 (e.g., modules within the DMS 302 that handled the request) "forget" that the request even occurred. In this manner, subsequently received requests are not influenced by (e.g., handled based on) previously processed requests.

In some examples, operation of the DMS 301 is stateless, but the DMS 301 can still provide a log of requests handled (e.g., using the logging sub-module). For example, a request log can be accessed during an audit of the system 300.

In some implementations, each facility system 302, 304 includes one or more local web modules 320, 330, one or more local host modules 322, 332, one or more local data cache modules 324, 334, and one or more vocabulary service modules 328, 338. In the depicted example, the facility system 302 includes one or more collector modules 326, and the facility system 304 includes one or more patient record (EMR) adapter modules 336.

In some examples, each of the web modules 320, 330 provides functionality as similarly discussed above with respect to the web module 310. More particularly, the web modules 320, 330 operate at a local level (e.g., local to the respective facility systems 302, 304), each performing request validation and user authentication, and routing requests to the respective local host modules 322, 332. For example, the web modules 320, 330 can receive requests from the respective mobile devices 102', 102", can validate the requests and authenticate the respective users/mobile devices, and route the requests accordingly. In some examples, each web module 320, 330 includes one or more sub-modules. Example sub-modules include a request validation sub-module, which validates received requests, a user authentication module, which authenticates an identity of the user and/or mobile device from which a request is received, and a request routing sub-module, which routes requests after validation and authentication.

In some examples, each of the local host modules 322, 332 provides functionality as similarly discussed above with respect to the host module 312. More particularly, the local host modules 322, 332 operate at a local level (e.g., local to the respective facility systems 302, 304), each orchestrating request processing. In some examples, the local host modules 322, 332 orchestrate request processing for requests received from the mobile device 102 through the DMS 301, and/or from the respective mobile devices 102', 102" through the respective local web modules 320, 330. In some examples, each local host module 322, 332 includes one or more sub-modules. Example sub-modules include a request parsing sub-module that parses received requests, a pipeline assembly sub-module, a pipeline processing sub-module, an operation execution sub-module, a data access sub-module, an access control sub-module and an encryption sub-module.

In some examples, each of the local data cache modules 324, 334 provides functionality as similarly discussed above with respect to the data cache module 314. More particularly, the local data cache modules 324, 334 operate at a local level (e.g., local to the respective facility systems 302, 304), each enabling access to and optional storage of detailed patient data/information used by other components of the system 300. In some examples, the each data cache module 324, 334 can operate in a pass-through mode and a reposed mode, as discussed above with respect to the data cache module 314. In the pass-through mode, the local data cache modules 324, 334 retrieve the patient data/information from one or more local data sources and passed the patient data/information onward for responding to the request. In some examples, it might be desired to improve retrieval performance. Consequently, the local data cache modules 324, 334 can store data identifiers and/or pointers in a persistent data store. When in the pass-through mode, the local data cache modules 324, 334 use the collector module 326 and the patient record adapter module 336, respectively, to perform the actual retrieval of patient data/information from local data source(s) (e.g., the patient record module 303 and the patient record module 305, respectively). In some examples, when in the pass-through mode, the local data cache modules 324, 334 can write data back to the respective patient record modules 303, 305.

In some examples, the patient data/information that is required to satisfy a request (e.g., from the mobile device 102', 102") cannot be directly accessed from the local data sources (e.g., the patient record modules 303, 305). In such examples, each local data cache module 324, 334 can operate in the reposed mode. In some examples, in the reposed mode, the local data cache module 324, 334 stores a detailed copy of the patient data/information in the persistent data store. That is, for example, stored patient data/information is stored at the local level, having been previously received from local data source(s) (e.g., the patient record modules 303, 305). In some examples, when a request is made for patient data/information in the reposed mode, the patient data/information is retrieved directly from the persistent data store (e.g., by the cache services sub-module).

In some implementations, the collector module 326 and the adapter module 336 are specific to the type of patient record module 303, 305, respectively. In the example of FIG. 3, the patient record module 303 can be accessed based on a particular messaging protocol. An example messaging protocol can include the Health Level 7 (HL7) messaging protocol. In some examples, patient data/information provided based on such messaging protocols is reposed by the data cache module 324. Consequently, requests for such data can be fulfilled based on operation of the data cache module 314 and/or the local data cache module 324 in the reposed mode, as discussed above. In some examples, changes to patient records in the patient record module 303 can trigger updating of reposed patient data/information by the data cache modules 314, 324. For example, the collector module 326 can automatically receive a message from the patient record module 303 in response to a change/updated, triggering updating/changing of reposed patient data/information.

In the example of FIG. 3, the patient record module 305 supports programmatic interface (e.g., API) access. In some examples, patient data/information provided through programmatic interfaces is passed-through the data cache module 314 and/or the data cache module 334. Consequently, requests for such data can be fulfilled based on operation of the data cache module 314 and/or the local data cache module 334 in the pass-through mode, as discussed above. In this manner, such patient data/information is not persisted by the data cache module 314, 334.

Although the example of FIG. 3 depicts facility systems 302, 304 having different types of patient record modules 303, 305, it is appreciated that facility systems can include any appropriate combination of types of patient record modules and any number of patient record modules (e.g., patient record modules 303, 305), and respective adapter modules (e.g., modules 326, 336). Further, although the example of FIG. 3 depicts two facility systems, implementations of the present disclosure are applicable in instances include any number of facility systems.

In some implementations, the vocabulary services modules 328, 338 perform translation between the vendor-specific vocabularies and a standard vocabulary. In this manner, patient data/information retrieved through the modules 303, 305 use standard vocabulary to be provided back to the mobile device 102 in a unified manner. For example, the patient record modules 303, 305 can each be provided by a respective third-party (e.g., a vendor) and can record data/information based on a vocabulary that is specific to the particular vendor. Consequently, data sources provided from different third-parties can refer to the same data/information or type of data/information using different terminology. In some examples, each vocabulary service module 328, 338 is specific to a respective patient record module 303, 305.

FIG. 4 is a more detailed view of the functional block diagram of FIG. 3, depicting additional components of the example system 300. In the depicted example, the DMS 301 further includes a patient list import module 400, a patient membership portal module 402, a patient matching service module 404, a provider management (mgmt) module 406, a patient information data store 408, and a directory information data store 410. In some examples, the patient information data store 408 stores patient demographic information 420, a data pointer cache 422, a patient-to-provider index 424 and a patient-to-facility index 426. In some examples, the directory information data store 410 stores a facility directory 430, a provider directory 432, and provider-to-facility index 434.

In some implementations, the patient list import module 400 enables initial and ongoing import of patient lists and patient demographic information for patients. In some examples, the patient list import module 400 provides an interface to receive a patient list, e.g., provided in a computer-readable document, and processes the patient list to populate the patient information data store 408 (e.g., the demographic information 420). In some examples, the patient membership portal module 402 provides an interface that enables users (e.g., an administrator) to establish relationships between patient data/information stored across healthcare continua and particular patients. In some examples, healthcare providers, facilities and/or facility systems across healthcare continua can be included in a healthcare organization (e.g., an accountable care organization (ACO)). In some examples, the patient membership portal module 402 enables a user to define relationships between multiple patient records (e.g., based on respective medical record numbers (MRNs)) to the healthcare organization. In some examples, relationship information defined through the patient membership portal module 402 can be stored in the patient information data store 408.

In some implementations, the patient matching service module 404 can be accessed by the host module 312 and the patient membership portal module 402. In some examples, the patient matching service module 404 can be accessed by an application executed on a mobile device (e.g., the mobile device 102) through the host module 312. In some examples, the patient matching service module 404 processes patient data and/or patient information to identify potential patient matches between disparate data sources (e.g., multiple, different EMRs across the healthcare continuum). In some examples, patient information associated with confirmed matches (e.g., confirmed by an administrator through the patient membership portal module 402, confirmed by a healthcare provider using a mobile device through the host module 312) can be stored in the patient information data store 408. In some examples, a patient matching user interface (UI) is provided (e.g., displayed on a mobile device) and can be used by a healthcare provider to search for patients and establish, record and/or confirm relationships between patient records in different systems that are related to a single patient.

In some examples, the demographics information 420 includes information that can be used to identify any patient that has been established in the system. In some examples, the demographics information 420 can be used to search for patients, discussed in further detail herein. Example demographics information can include name, age and/or gender. In some examples, the data pointer cache 422 stores identifiers associated with detailed patient data. In some examples, the identifiers point to particular data stores, in which to be retrieved patient data/information is stored. In this manner, retrieval performance (e.g., speed) can be improved. In some examples, the patient-to-provider index 424 maps particular patients to one or more healthcare providers, and/or particular healthcare providers to one or more patients. For example, a patient can be treated by a plurality of healthcare providers (e.g., members of a patient care team, discussed below). As another example, a healthcare provider can treat a plurality of patients. In some examples, the patient-to-facility index 426 maps particular patients to one or more facilities and/or facility systems. In some examples, a patient can be mapped to particular facilities based on respective MRNs of the patient at the respective facilities. For example, a healthcare continuum for a particular patient can include a hospital and a clinic. In this example, the patient-to-facility index can map the patient to the MRN of the hospital and the MRN of the clinic.

In some implementations, the provider management portal module 406 provides an interface (e.g., web portal) to enable members of a healthcare organization (e.g., ACO) to update healthcare provider directory information and/or healthcare provider-to-facility relationships. For example, a physician can be associated with one or more facility systems of the healthcare organization and credentials (e.g., for log on and/or authentication) can be provided to enable the physician to access patient data/information provided from the one or more facility systems.

In some examples, the facility directory 430 provides a directory of the facilities interfaced to by the system (e.g., the DMS 301). In some examples, the facility directory 430 also provides configuration parameters to enable communication (messaging) between the system and computing devices associated with the respective facilities. In some examples, the provider directory 432 includes a directory of healthcare providers (e.g., nurses, physicians, specialists, and the like) that are able to access patient data/information through the system (e.g., the DMS 301). In some examples, the provider-to-facility index 434 maps each healthcare provider (e.g., in the provider directory) to one or more facilities. For example, a healthcare provider can treat patients at multiple facilities. In some examples, the provider-to-facility index 434 securely stores credentials of healthcare providers for facilities that the healthcare provider is mapped to. For example, a healthcare provider can have first credentials for accessing patient data/information at a first facility, and can have second credentials for accessing patient data/information at a second facility. In some examples, the provider-to-facility index 434 supports single sign-on functionality discussed in further detail herein.

An example data flow will be discussed to illustrate implementations of the present disclosure. It is appreciated that implementations of the present disclosure are equally applicable to other data flows. The example data flow can be initiated in response to a request received from a mobile device (e.g., the mobile device 102). In some examples, the request includes a user identifier, a device identifier, a patient identifier, patient data identifiers, patient information identifiers and additional data identifiers. In some examples, the user identifier can be used to determine the particular user that has issued the request, and the device identifier can be used to determine the particular device that transmitted the request. In some examples, the patient identifier identifies the particular patient that is the subject of the request, the patient data identifiers identify the particular patient data that has been requested, the patient information identifiers identify the particular patient information that has been requested, and the additional data identifiers identify additional data that has been requested. For example, the patient data identifiers can indicate that patient vital data has been requested, and the additional data identifiers can indicate that vitals alarm data and vital data trend visualizations have also been requested.

In the example data flow, the web module 310 receives the request and processes the request to validate the request and to authenticate the user, who submitted the request (e.g., based on the user identifier and/or the device identifier). Upon validation and authentication, the web module 310 provides the request to the host module 312. The host module 312 processes the request, as discussed above. In some examples, it can be determined that patient data/information required to fulfill the request can be provided from the data cache module 314 (e.g., reposed mode). In such examples, the patient data/information is provided to the host module 312 from the data cache module 314. In some examples, it can be determined that that patient data/information required to fulfill the request is to be retrieved from one or more data sources across a healthcare continuum of the patient (e.g., federated mode).

In some examples, if patient data/information required to fulfill the request is to be retrieved from one or more data sources across the healthcare continuum (e.g. federated mode), request information (e.g., assembled by the host module 312, as discussed above) is provided to the adapter module 316 by data cache module 314. In some examples, the adapter module 316 accesses information stored in the directory store 410 to request data from one or more facility systems (e.g., the facility system 304). For example, the adapter module 316 can be aware of which facility systems to retrieve patient data/information from (e.g., based on the patient-to-facility index 426) and can access the provider-to-facility index 434 to retrieve user credentials for the particular provider (e.g., user that issued the request). In this manner, the adapter module 316 can provide appropriate user credentials to respective facility systems for patient data/information retrieval.

In some examples, the adapter module 316 sends requests to identified facility systems, each request identifying patient data/information and providing appropriate user credentials. In some examples, respective host modules (e.g., the host module 332) of the facility systems receive the requests from the adapter module 316, and can process the requests as similarly discussed above with reference to the host module 312. The respective host modules fulfill the requests and provide the requested patient data/information back to the adapter module 316. In some examples, the adapter module 316 provides the retrieved patient data/information to the host module 312, which completes processing of the request, as discussed above, and provides a response to the mobile device that issued the request.

As discussed at the outset, the present disclosure provides a healthcare provider, or user of the mobile device 102, with secure, remote access to patient data and/or patient information. Example patient data can include physiological data. In some examples, physiological data can be obtained from patient monitoring device(s). In some examples, physiological data can be obtained by a local healthcare provider (e.g., a nurse, or physician measuring blood pressure, temperature, heart rate). In some examples, physiological data can be recorded in one or more patient records (e.g., EMRs). In the example case of a maternity patient, patient data can include delivery progress information such as cervical exam status, membrane status, gravida, para, epidural status, and/or whether the patient is attempting a vaginal birth after cesarean (VBAC). In some examples, the term patient information refers to information corresponding to a particular patient that is, for example, input into the information system 142 by the local healthcare provider. Example patient information can include the patient's name, the name of the doctor(s) assigned to the patient, the nurse(s) assigned to the patient, a facility identification, a patient bed identification, a summary of patient data, and/or chart annotations. The term patient information can also refer to patient information provided from one or more patient records (e.g., EMRs).

The patient data and/or patient information provided to the remotely located user can be provided as real-time data, and/or as historical data and information. The patient data and/or patient information is communicated between the mobile device 102 and the DMS 160, 160' using a secure connection that is established over the network 106. A secure log-in, or sign-on process is provided, which is preferably compliant with the provisions of the Health Insurance Portability and Accountability Act (HIPAA). The secure sign-on authenticates the identity of the user of the mobile device 102 based on a unique user ID and password combination. Both the user ID and the password must be correct in order to establish the secure communication between the mobile device 102 and the DMS 160, 160'.

In some examples, a census, or patient list is provided, which captures a variety of the information and/or data described herein that is associated with each of one or more monitored patients 150. Strip charting is also provided, in which patient data and/or information can be presented to the user in graphical form. In the example case of a maternity patient, a fetal strip and maternal contraction information can be provided for a particular patient 150. More specifically, the particular patient 150 is selected from the patient list, and the patient information and/or data is subsequently presented. The presented information and/or data can include a fetal strip and maternal contraction waveform, the patient name, the hospital name, the patient room and/or bed number, and the date and time. The strip charting can provide a real-time view of the patient data, as well as a historical view of the patient data. More specifically, the waveform display can be updated in real-time, such that the user of the mobile device 102 observes the patient data as it occurs and/or is recorded. The user can scroll through the waveform display, to view historical patient data, as described in further detail below.

Several navigation features can be provided that enable the user to manipulate a view of the waveform display. In some implementations, the user can zoom in/out of the displayed image. In this manner, the user can view very specific waveform information, and/or other waveform micro-characteristics by zooming in, for example, and/or can view patterns or other waveform macro-characteristics by zooming out, for example. In some implementations, the user can scroll forward or backward through the waveform display. In this manner, the user can view historical patient data.

A patient data display can also be provided. In some implementations, the patient data display can overlay the strip charting described herein. In other implementation, the patient data display can be provided as an overlay, and/or as a separate display. The patient data display can include, but is not limited to, the patient's name, age, fetal gestation, gravida, parity, cervical exam information, and physician name.

Implementations of the present disclosure can be realized on any one of a number of operating systems, or platforms 302 associated with the particular mobile device 102. Example platforms include, but are not limited to, RIM Blackberry, Apple iOS and/or OS X, MS Pocket PC, Win Mobile (Pocket PC, Smartphone), Win Mobile (standard, professional) and/or any other appropriate platforms (e.g., Google Android, and Hewlett-Packard WebOS, Microsoft Windows, Unix, Linux).

As discussed in detail herein, implementations of the present disclosure are directed to systems and methods of providing integrated and unified views of patient data and patient information from disparate data sources and/or products. More particularly, implementations of the present disclosure provide integrated and unified views of patient data and patient information retrieved from across a healthcare continuum. In some examples, the healthcare continuum can include a plurality of disparate clinical data sources. In some examples, a clinical data source can correspond to one or more categories of healthcare services. Example categories can include emergency medical services (EMS), outpatient services, inpatient services, ambulatory services, post-acute services, home services and stand-alone services. Example EMS can include emergency departments (e.g., emergency room (ER) of a hospital), urgent care facilities and transport (e.g., ambulance). Example outpatient services and/or inpatient services can include hospitals and/or critical access hospitals (CAHs). Example ambulatory services can include clinics, physicians groups/offices, surgery centers and pre-acute care. Example post-acute services can include skilled nursing facilities, long-term care hospitals, rehabilitation centers and home healthcare. Example stand-alone services can include imaging centers (e.g., MIR), oncology centers, laboratories, virtual call centers and retail clinics.

Figure 5:
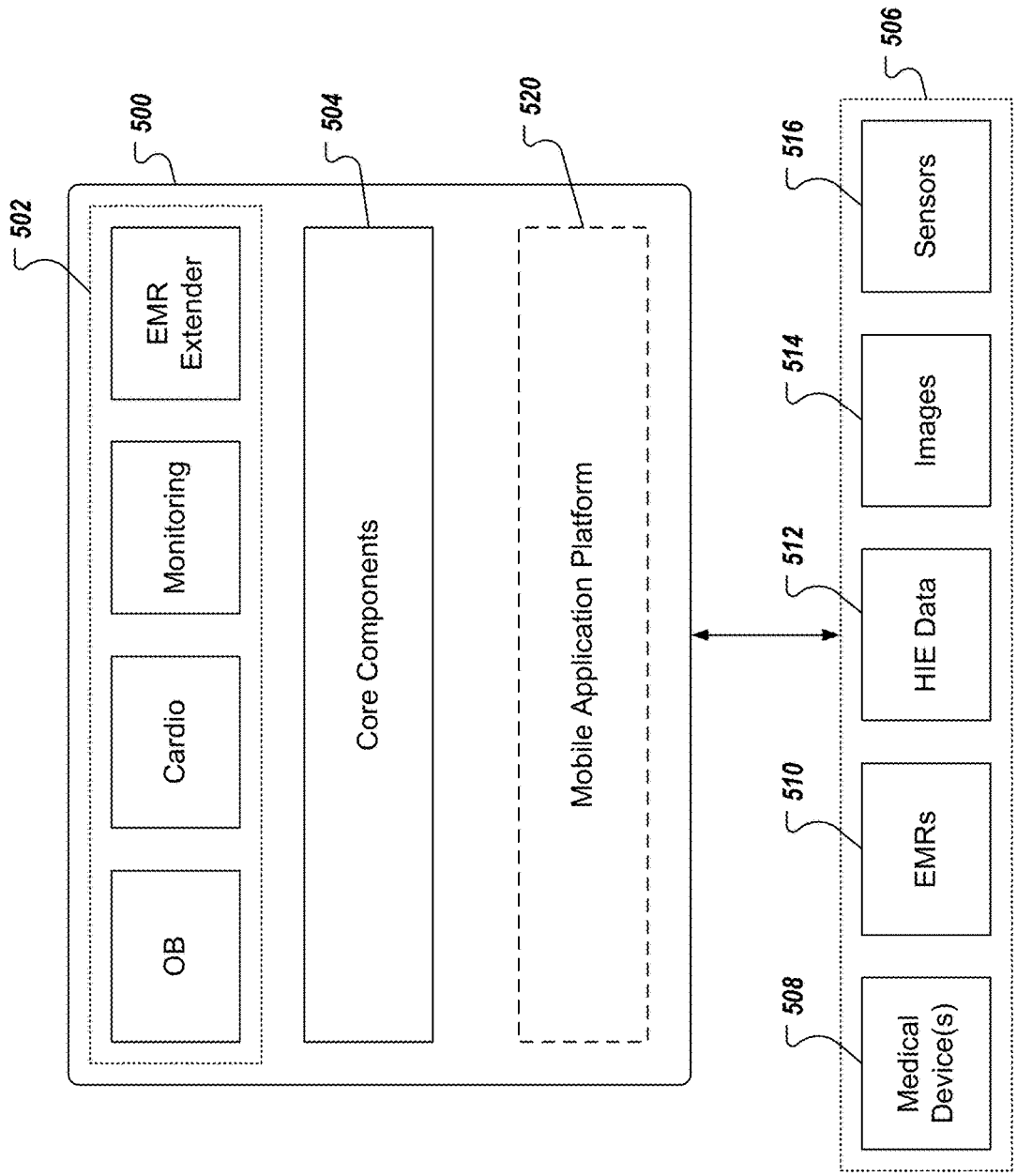
FIG. 5 depicts an example platform for providing integrated and unified views of patient data and patient information.

FIG. 5 depicts an example platform 500 for providing integrated and unified views of patient data and patient information. The example platform 500 includes one or more product applications 502 and core components 504. The example platform enables the transfer of patient data/information to/from one or more data sources 506 for display on a mobile device (e.g., the mobile device 102). In some examples, the example platform 500 is provided as one or more computer-executable programs that are executed using one or more computing devices (e.g., the DMS 160, 160'). Example data sources 506 can include one or more medical devices (e.g., bedside monitors), one or more EMRs, health information exchange (HIE) data 512, image data 514 (e.g., x-ray data), and sensor data 516.

In some implementations, the example platform 500 can include a mobile application platform 520. An example mobile application platform 520 can include the mobile application platform disclosed in U.S. application Ser. No. 13/716,974, filed Dec. 17, 2012, and which claims the benefit of U.S. Prov. App. No. 61/579,954, filed Dec. 23, 2011, the disclosures of which are expressly incorporated herein by reference in their entireties.

In some examples, the mobile application platform 520 separates native graphical user interface (GUI) and operating system components from the application logic. In this manner, the mobile application platform 520 translates and interprets application logic into the native languages of each operating system of mobile devices to/from which patient data/information is to be transferred, and embraces the unique properties, features, function, and usability of each operating system. In some implementations, the mobile application platform 520 embodies a template-based approach, where one or more templates are provided, each template corresponding to a view of patient data/information that is to be presented on a mobile device. In some examples, and as discussed in further detail herein, default templates can be provided, which provide default views of patient data/information. In some examples, custom templates can be provided, and can include templates customized by a user of a mobile device.

In some examples, the mobile application platform 520 processes patient data/information based on a template that defines a view to be displayed on the mobile device. In some examples, the mobile application platform 520 generates instructions for rendering graphics based on the patient data/information and the template, and provides instructions to the mobile device, the mobile device executing the instructions to provide the template-based view of the patient data/patient (e.g., rendering the patient data/information in a view displayed on the mobile device).

In some examples, the product applications 502 can include medical software applications that enable mobility in healthcare. For example, products can enable patient information and patient data (e.g., waveforms and other critical data from EMRs, bedside monitors and devices, pharmacy, lab, and other clinical information systems) to be securely and natively accessed by healthcare provides on mobile devices. Example products can include an obstetrics (OB) product (e.g., AirStrip OB provided by AirStrip Technologies, LLC), a cardiology product (e.g., AirStrip CARDIO provided by AirStrip Technologies, LLC), a patient monitoring product (e.g., AirStrip PATIENT MONITORING provided by AirStrip Technologies, LLC), and an EMR extension product (e.g., AirStrip EMR EXTENDER provided by AirStrip Technologies, LLC).

Figure 6:
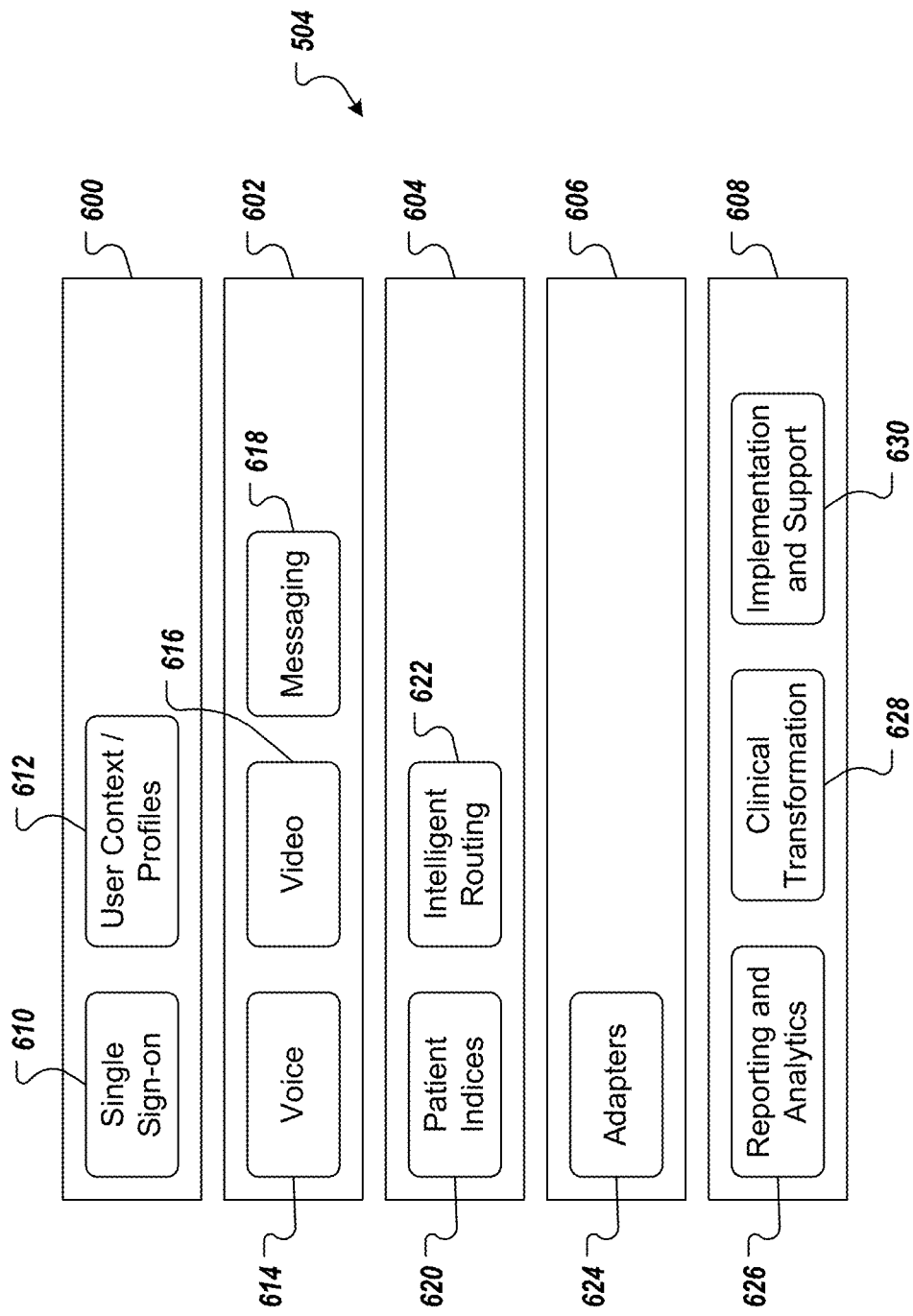
FIG. 6 depicts example components and sub-components that can be included in core components of FIG. 5.

FIG. 6 depicts example components and sub-components that can be included in the core components 504 of FIG. 5. In some examples, each component and/or sub-component can be provided as one or more computer-executable programs that can be executed using one or more computing devices (e.g., computing devices of the DMS 160, 160' of FIGS. 1 and 2). In some examples, the core components provide secure data access and data transport, single sign-on and profile/context management, interoperability (data adapters and interfaces), intelligent message routing, master patient indices (e.g., EMPI) and care collaboration.

In the depicted example, the core components 504 include a security component 600, a care coordination and collaboration interfaces component 602, a data and workflow integration component 604, a data source adapters component 606 and a services component 608. In the depicted example, the security component 600 includes a single sign-on sub-component 610 and a user context/profiles sub-component 612. In the depicted example, the care coordination and collaboration interfaces component 602 includes a voice sub-component 614, a video sub-component 616 and a messaging sub-component 618. In the depicted example, the data and workflow integration component 604 includes a patient index (or indices) component 620 and an intelligent routing sub-component 622. In some examples, the data source adapters component 606 can include adapter services sub-components 624 (e.g., the adapter services module 324 of FIG. 3). In the depicted example, the services component 608 includes a reporting and analytics sub-component 626, a clinical transformation sub-component 628 and an implementation and support sub-component 630.

In some examples, the single sign-on sub-component 610 supports single sign-on functionality, discussed herein. In some examples, a user can be authenticated once (e.g., by providing log-in credentials to an application executed on a mobile device) and can be provided access to data across a plurality of data sources, without being authenticated for each data source individually. In some examples, the user context/profiles sub-component 612 supports user-specific customizations based on a context of the user and/or a profile of the user, as discussed in further detail herein. Example contexts can include the user being an attending physician at one hospital and a part-time physician at another hospital. In some examples, one or more profiles can be associated with the user, each profile reflecting one or more customizations associated with the particular user. For example, the user can customize a default view that can be displayed on a mobile device, to provide a customized view. Consequently, after the user is authenticated, one or more user-defined (user-customized) views can be provided to the mobile device.

In some examples, the care coordination and collaboration interfaces component 602 supports collaboration between members of a patient care team. For example, a patient care team can include a physician, a consultant, a specialist, an intensivist and a nurse. In some examples, the voice sub-component 614 provides voice-based collaboration between care team members (e.g., teleconferencing). In some examples, the video sub-component 616 provides video-based collaboration between care team members (e.g., video conferencing). In some examples, the messaging sub-component 618 provides messaging-based collaboration between care team members (e.g., SMS/MMS text messaging). In some examples, the care coordination and collaboration component 602 provides security in remote collaboration between care team members (e.g., secure teleconferencing, secure video conferencing and/or secure messaging).

In some examples, the data and workflow integration component 604 integrates data from a plurality of data sources and routes data for display on mobile devices. In some examples, the patient index (or indices) component 620 provides one or more indices for mapping users to facilities and/or patients. In some examples, one or more indices can be provided to associate a user (e.g., a physician) with a facility or multiple facilities (e.g., hospitals), to associate a patient with a facility or multiple facilities, and/or to associate a user with one or more patients. In some examples, an index can be based on an ACO. In some examples, the ACO includes one or more healthcare providers across a healthcare continuum and can provide cross-access to patient data/information. In some examples, the intelligent routing sub-component 622 provides intelligent routing functionality, discussed above.

In some examples, the data source adapters component 606 provides adapter functionality. In the depicted example, the services component 608 includes a reporting and analytics sub-component 626, a clinical transformation sub-component 628 and an implementation and support sub-component 630.

As discussed in further detail herein, patient data and patient information can be provided from one or more disparate patient data sources (e.g., examples depicted in FIG. 5). In some examples, a patient can be associated with one or more healthcare services across the healthcare continuum. Consequently, and for each patient, patient data and patient information can be distributed across the healthcare continuum. For example, a patient can be taken to a hospital by EMS (e.g., ambulance), can be treated in an emergency department of the hospital (e.g., ER), can stay in the hospital on an inpatient basis, can frequent a rehabilitation center (e.g., physical therapy), can be undergoing home healthcare (e.g., home nursing care), and patient samples can be sent to a laboratory for analysis (e.g., blood analysis provided by an external laboratory). In this example, treatment of the particular patient touches multiple facilities across the healthcare continuum, and each facility can generate its own patient data, patient information and patient records (EMRs).

In general, an EMR can be described as a digital medical record provided as an electronic document that can be processed (e.g., read from/written to) by one or more computer programs executed by one or more computing devices. Further, each entity or organization (e.g., clinic, hospital, physician, rehabilitation center, laboratory) that treats a patient can include its own, stand-alone information system that provides an EMR that is specific to the information system. Consequently, multiple, disparate EMRs can be provided for a single patient across the healthcare continuum. Within the context of the example above, a first EMR can be provided for the patient by an ambulance service that transported the patient to the hospital, a second EMR can be provided for the patient by the hospital, a third EMR can be provided for the patient by the rehabilitation center and a fourth EMR can be provided for the patient by a nursing company that is providing home nursing care to the patient. In some examples, and as noted above, EMRs can be generated from disparate information systems. Consequently, format and syntax of one EMR can be different from the format and syntax of another EMR.

In some examples, historical patient data and information can be provided for viewing by a healthcare provider, as well as providing real-time patient data for viewing to the healthcare provider. Extending the example above, the patient can be re-admitted to the hospital on an inpatient basis and can be connected to one or more patient monitoring devices that generate patient physiological data based on patient physiological activity. In accordance with implementations of the present disclosure, and as discussed in further detail herein, patient data and information from one or more of the first EMR, the second EMR, the third EMR and the fourth EMR, as well as real-time patient data can be provided for display to a healthcare provider (e.g., a physician attending to the patient) on a mobile device in an integrated and unified manner. For example, real-time and/or historical patient physiological data can be provided for display by multiple products (e.g., a cardiology product and a patient monitoring product). Implementations of the present disclosure enable integration and unification of the patient physiological data across the products.

In accordance with implementations of the present disclosure, patient data can be displayed to a user of a computing device. In some implementations, the user provides log-in credentials to an application that is executed on the mobile device. For example, the application can open and can provide a log-in screen for the user to provide credentials. In some examples, the credentials can include a personal identification number (PIN). If the PIN is not authenticated (e.g., the user-input PIN is not the same as a pre-stored PIN), an error is displayed. If the PIN is authenticated (e.g., the user-input PIN is the same as a pre-stored PIN), a sites screen or a base screen can be displayed. In some examples, authentication can be provided based on a personal identifier (e.g., the PIN) and another identifier. In some examples, another identifier can include an identifier that is unique to a mobile device that the user is using. For example, the PIN and a unique device identifier can be provided for authentication.

Figure 7:
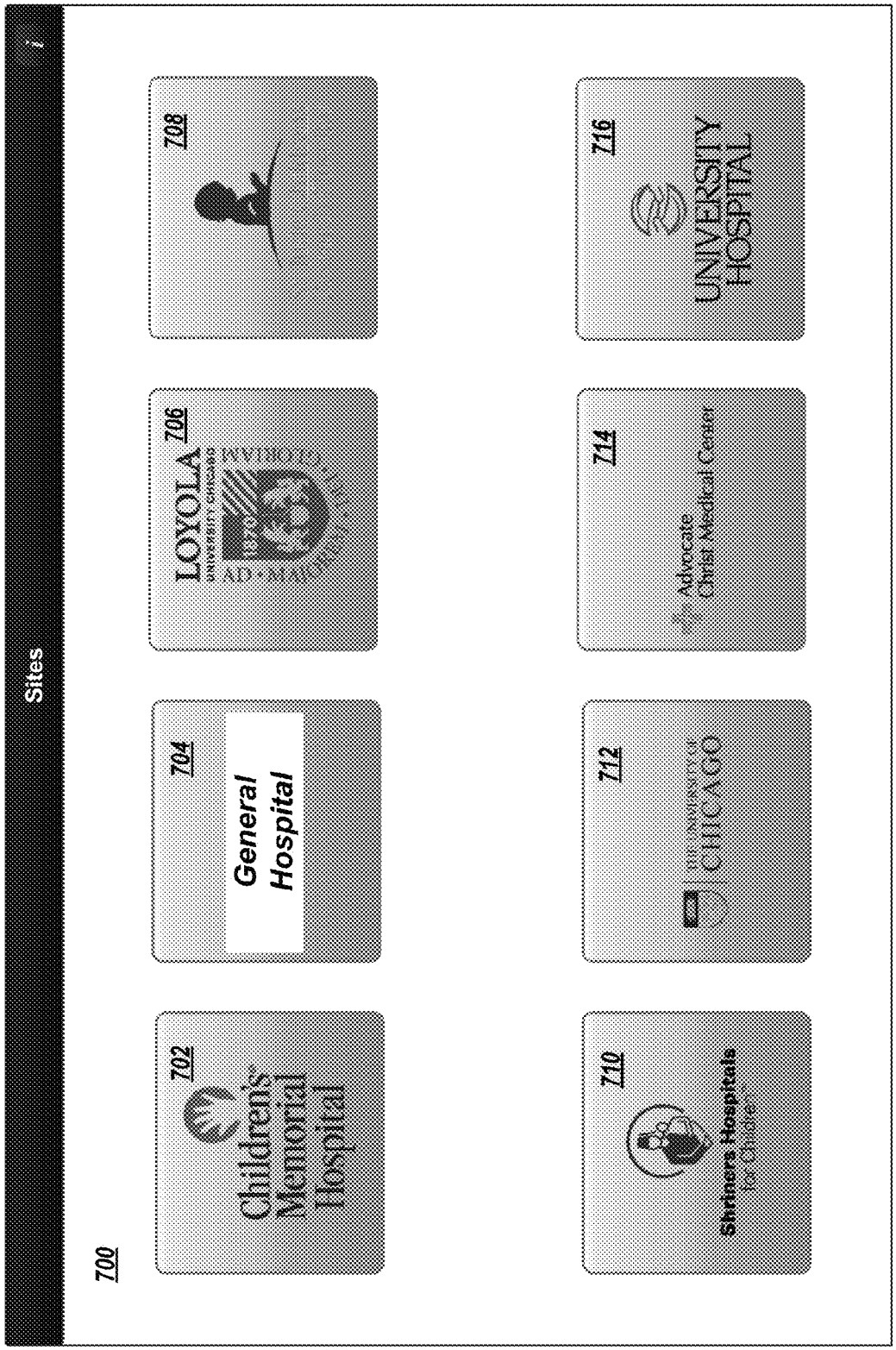
FIGS. 7-10 depict example graphical user interfaces (GUIs) for providing integrated and unified views of patient data and patient information in accordance with implementations of the present disclosure.

FIG. 7 depicts an example sites screen 700. In some implementations, the sites screen 700 provides a GUI including one or more site icons that can be selected (e.g., clicked on) by the user. In some examples, a site can include a specific facility (e.g., hospital clinic), a system of facilities (e.g., a hospital system including one or more hospitals, one or more clinics, and/or one or more laboratories, and the like). In some examples, an index (e.g., a user-facility index) can be accessed based on an identifier associated with the user, to determine the one or more site icons that are to be displayed to the user. In some examples, in response to the PIN being authenticated, an identifier associated with the user can be provided to the DMS 160', for example, by the mobile device 102 (see FIGS. 1 and 2). In some examples, the DMS 160' stores an index (e.g., a user-facility index) that is accessed based on the identifier. In some examples, the index maps the identifier associated with the user to one or more facilities that the user is associated with. In response, the DMS 160' provides instructions to the mobile device 102 to display the sites screen 700 including the one or more site icons 702, 704, 706, 708, 710, 712, 714, 716, each site icon being a graphical representation of a facility of facilities that the user is associated with.

In some implementations, and as noted above, the user can be associated with more than one site (e.g., 702, 704, 706, 708, 710, 712, 714, 716). In some implementations, the user is affiliated with a single site, which is included in a network that includes a plurality of inter-communicating sites associated therewith. In some examples, a site can include a medical center, a dispensary, a hospital, an infirmary, a surgery center, an ambulatory setting, a nursing home, a rest home, a sanatorium, a sanitarium, or any other appropriate healthcare facility. In some implementations, the site screen 700 can provide a summary of each site and/or specific sites, with which the user is associated. In some examples, a site summary can include a plurality of selectable icons (e.g. a site access icon, a site information icon, a patient information icon, etc.). In some implementations, each site summary can include attributes (e.g. patient counts).

User input can be provided to the site screen 700, the user input indicating a selection of a site icon of the one or more site icons. In some examples, user input can include touching of a touchscreen display with a digit (e.g., finger), a stylus, and/or other pointing device, as well as with a digital cursor and/or a keypad.

In some implementations, a base screen can be displayed. In accordance with implementations of the present disclosure, and as discussed in further detail herein, the base screen can include a menu. In some examples, the menu provides a GUI, through which the user can request display of patient data/information. In some examples, the menu is a user-specific menu. In some examples, the menu is specific to one or more user contexts. In some examples, the menu is specific to a site selected by the user. In some examples, the base screen is displayed in response to the PIN being authenticated. In some examples, the base screen is displayed in response to user input to the sites screen.

In accordance with implementations of the present disclosure, the menu is provided as a slide-out menu that is animated in response to user selection of an icon. In some examples, the menu can be animated such that the menu appears to slide-out from an edge of the base screen (e.g., left-side edge). In some examples, the menu is animated such that the menu appears to slide-in to the edge of the base screen in response to user selection of an icon from the menu.

In accordance with implementations of the present disclosure, the menu can include icon groups. In some examples, the icon groups can be provided as default icon groups. For example, a default icon group can be displayed in the menu, the default icon group being agnostic to the particular user (e.g., displayed for any user). In some examples, the icon groups can include user-customized icon groups. For example, the menu can include a user-customized icon group that is specific to (e.g., that was defined by) the user. In some examples, the icon groups can include user-specific and/or site-specific icon groups. For example, an icon group can include a workflow icon group that is specific to the role of the user (e.g., an attending physician) at a specific facility.

Figure 8:
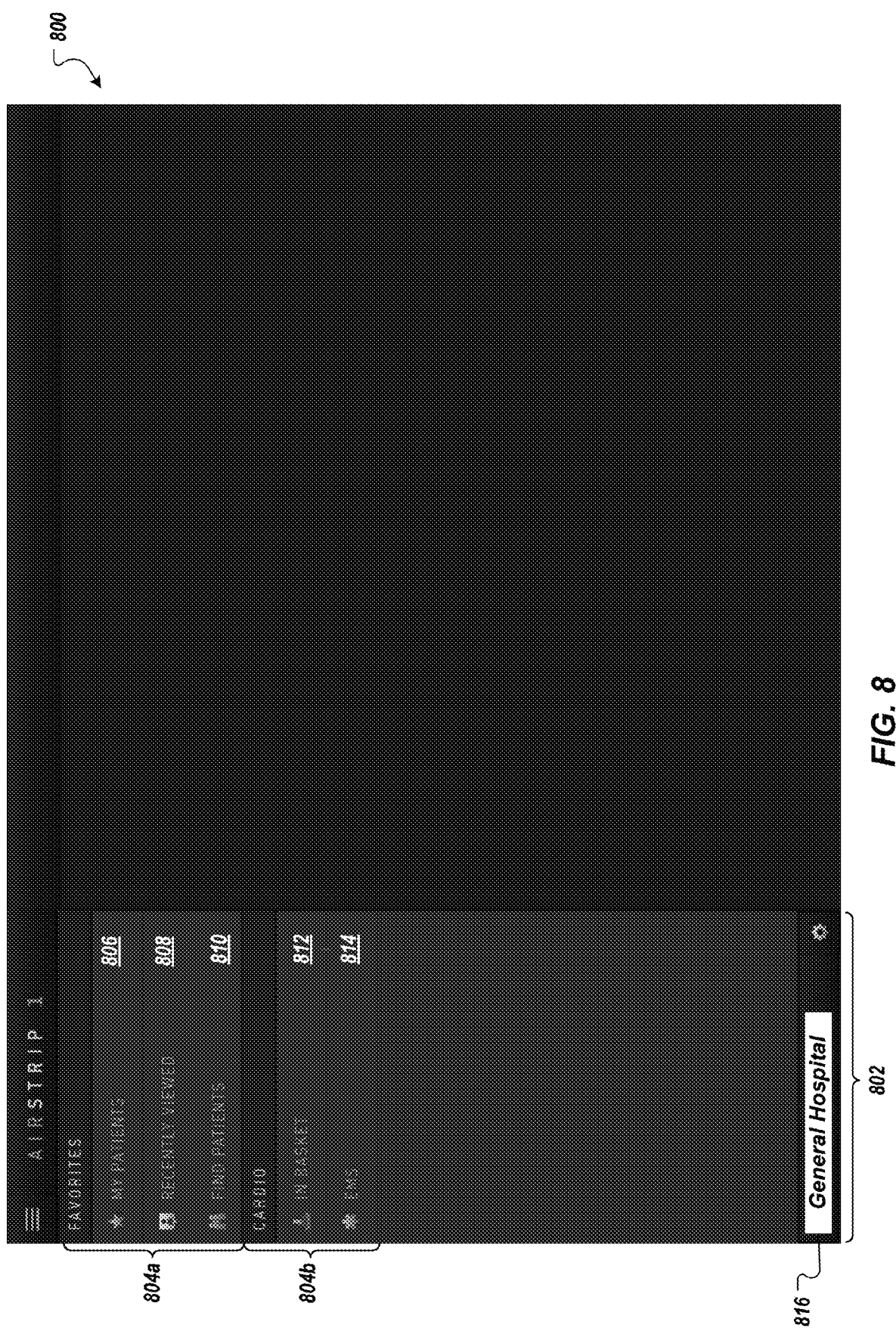

FIG. 8 illustrates an example screen-shot of a base screen 800 that includes a menu 802. The example base screen 800 of FIG. 8 is user-specific and site-specific. For example, the base screen 800 can be displayed in response to user selection of a site icon (e.g., the site icon 704 of FIG. 7). Consequently, a site identifier 816 can be provided to indicate the site, to which the menu 802 is specific. In some examples, a request for the base screen is provided to the DMS 160' in response to user selection of an icon from the sites screen 700. In some examples, the request indicates the site that was selected. In some examples, a user-facility index can be accessed to determine a configuration of a menu to be displayed in the base screen. For example, and for a given site (facility), the user can have an associated profile, user-defined patient groups, context-specific workflows and/or facility-specific workflows. Consequently, the DMS 160' can provide instructions for displaying a user-specific, site-specific base screen, such as the example base screen 800 of FIG. 8. More particularly, the instructions can include instructions for displaying a user-specific, site-specific menu 802 for the base screen 800.

In the depicted example, the menu 802 provides icons for initiating respective displays of patient data/information. In the menu 802, the icons are displayed in icon groups, or menu groups 804a, 804b. It is appreciated that more or fewer icon groups can be displayed. In the example of FIG. 8, the icon group 804a can be provided as a default icon group. For example, the icon group 804a includes icons "My Patients" 806, "Recently Viewed" 808, and "Find Patients" 810. In some examples, the icons 806, 808, 810 are default icons. That is, for example, the icons 806, 808, 810 are not specific to the user and/or the facility (e.g., the icons 806, 808, 810 are displayed regardless of the particular user and/or the particular facility). In some examples, the icon group 804a can be customized by the user. For example, the user can define a patient group (e.g., "My Cardio Patients," "My OB Patients") and can associate one or more patients with the group. Consequently, an icon that is representative of a user-defined group can be displayed in the icon group 804a.

In the example of FIG. 8, the icon group 804b can be provided as a user-specific and facility-specific icon group. For examples, the icon group 804b can be representative of a workflow (e.g., "Cardio") associated with the user at the particular facility (e.g., as indicated by the identifier 816). Consequently, the icon group 804a can include icons that are relevant to the particular workflow. In the depicted example, the icon group 804b includes an "In Basket" icon 812 and an "EMS" icon 814. In some examples, a workflow can include one or more tasks to be performed by the user as part of the user's role at a particular facility.

In some implementations, a request can be provided to the DMS 160' in response to user selection of an icon from the menu 802. In the example of FIG. 8, the user can select the "My Patients" icon 806. In response, a request can be provided to the DMS 160', the request indicating a request for a list of all patients that the user is associated with. The DMS 160' can provide a response that includes instructions to display a list of all patients associated with the user and can include patient data/information for display. In some examples, and in response to the user selection of the "My Patients" icon 806, the menu 802 is animated to slide-in to the edge of the screen.

Implementations of the present disclosure enable remote execution of patient-associated tasks. In some examples, patient-associated tasks can be time sensitive. For example, review and confirmation of a patient ECG by a cardiologist can be required to be executed within a pre-determined time period. Although review and confirmation of a patient ECG will be used herein as an example patient-associated task, it is contemplated that implementations of the present disclosure are applicable to other appropriate patient-associated tasks. In some examples, if a patient-associated task is not executed within the pre-determined time period associated costs will not be reimbursed (e.g., by a health insurance provider, by government administered programs). Consequently, implementations of the present disclosure provide time-sensitive, patient-associated tasks for display on mobile devices, and enable users to remotely execute such tasks, as discussed in further detail herein.

In some implementations, information associated with one or more patient-associated tasks can be provided from one or more back-end systems (e.g., ECG management system, perinatal system, patient intake system, any appropriate clinical information system). In the example context, ECG information can be provided from an ECG management system. In some examples, patient-associated tasks that are within the pre-determined time period are displayed to a user of a mobile device. In some examples, an initial timestamp of a patient-associated task can be compared to a current time. In some examples, if a difference between the current time and the initial timestamp is below a threshold time (e.g., the pre-determined time period), a graphical representation of the patient-associated task is displayed to the user. In the example context, it can be provided that an ECG must be reviewed and confirmed within 24 hours of the ECG having been taken. Consequently, if a difference between a current time, and the time at which the ECG was taken exceeds a threshold time (e.g., 24 hours), a graphical representation of the patient-associated task is not displayed to the user.

In some implementations, graphical representations of time-sensitive, patient-associated tasks can be displayed to the user in a first "Tasks" screen (first screen). In some examples, the first screen displays graphical representations of patient-associated tasks that are still within the pre-determined time period. In some examples, the first screen exclusively displays graphical representations of patient-associated tasks that are still within the pre-determined time period. In some implementations, graphical representations of time-sensitive, patient-associated tasks can be displayed to the user in a second "Tasks" screen (second screen). In some examples, the second screen displays graphical representations of patient-associated tasks that are already outside of the pre-determined time period. For example, although a patient-associated task was not completed within the pre-determined time period, the patient-associated task is still indicated to the user, such that the patient-associated task can still be executed by the user. In some examples, the second screen displays graphical representations of patient-associated tasks that are outside of the pre-determined time period. In some examples, the second screen displays graphical representations of patient-associated tasks that are still within the pre-determined time period, and graphical representations of patient-associated tasks that are outside of the pre-determined time period.

In some implementations, and as depicted below with reference to FIGS. 9 and 10, the user can perform patient-associated tasks on the mobile device. In some examples, in response to the user performing a patient-associated task, a signal and/or data can be provided to a back-end system. In this manner, the back-end system can record when the patient-associated task was executed and/or determine whether the patient-associated task was completed with the pre-determined time period.

Figure 9:
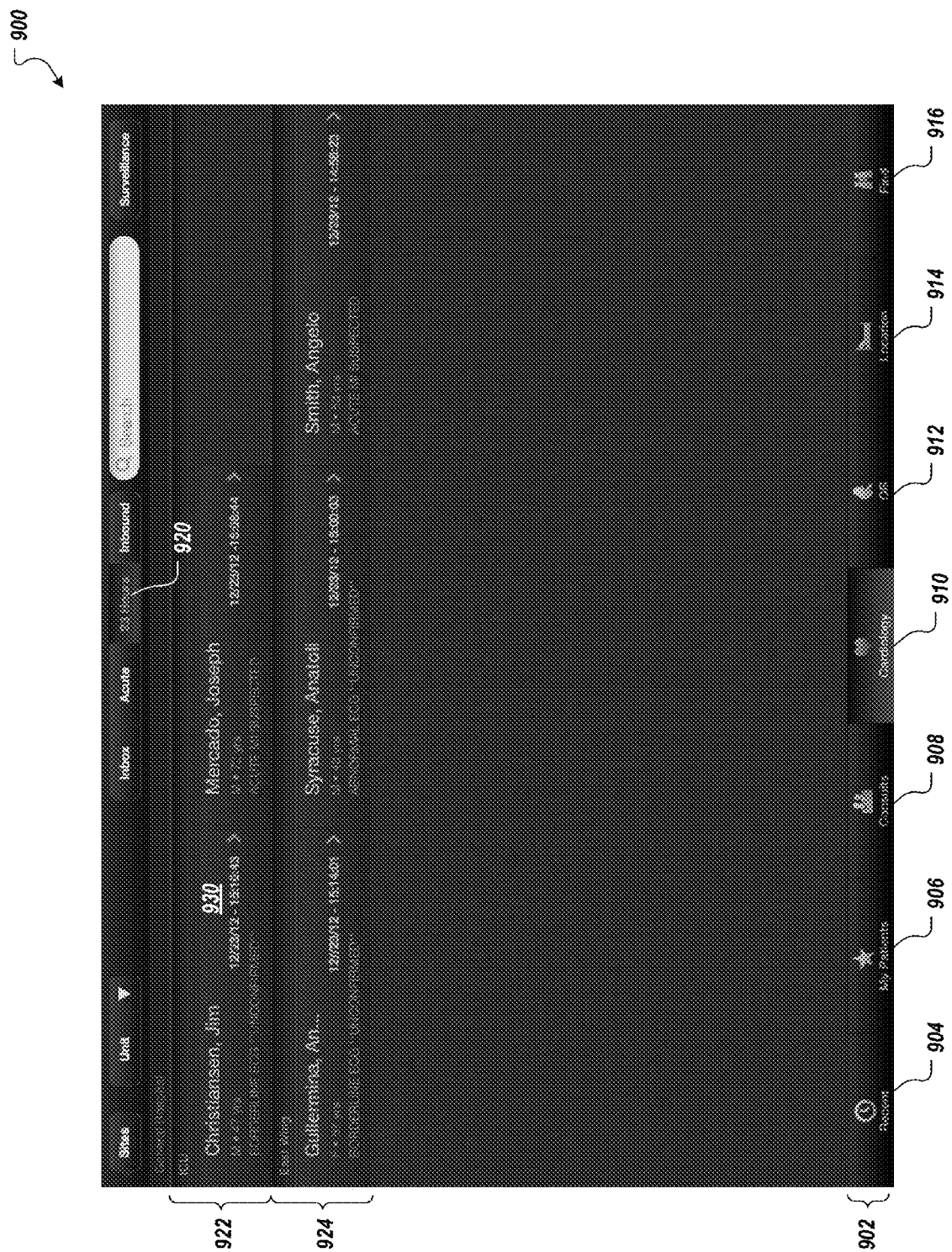
Figure 10:
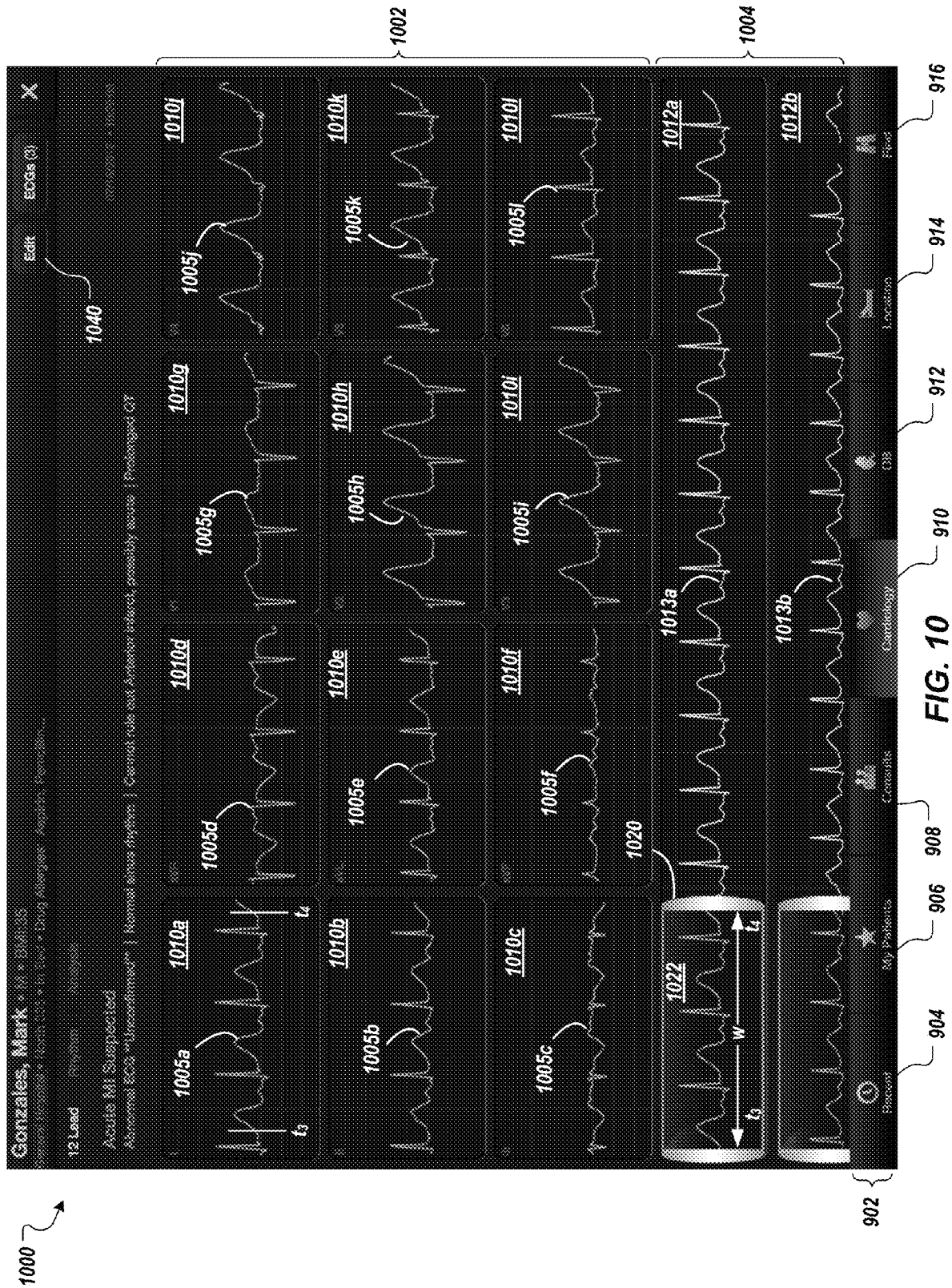

FIGS. 9 and 10, discussed in further detail below, depict an example context for remote display and execution of time-sensitive, patient-associated tasks. The example context includes reviewing and confirming one or more pending ECGs. In some example, requests and/or ECG information can be provided from an appropriate information source (e.g., an ECG management system).

FIG. 9 illustrates an example screenshot of a "Time-Sensitive Tasks" screen 900 that can be displayed in response to user selection of a "Cardiology" icon in a base screen, and a time-sensitive icon. In this example, the screen 900 is user-specific and site-specific (e.g., specific to General Hospital), and includes a menu 902 that provides icons for initiating respective displays of location maps and patient data/information. In the example menu 902, "Recently Viewed" icon 904, a "My Patients" icon 906, a "Consults" icon 908, a "Cardiology" icon 910, an "OB" icon 912, a "Location" icon 914, and a "Find Patients" icon 916. The screen 900 further includes a time-sensitive icon 920.

In the depicted example, the icon 910 and the icon 920 are selected. Consequently, graphical representations of time-sensitive, patient-associated tasks are displayed. More particularly, the screen 900 provides icon groups 922, 924, each icon group 922, 924 including one or more patient icons 930 that represent a time-sensitive, patient-associated task. For example, the patient icons 930 represent time-sensitive, patient-associated tasks that are still within a pre-determined time period. In the depicted example, the a pre-determined time period includes 23 hours, indicating that each patient-associated task has been initiated within the last 23 hours and still needs to be completed. In some examples, a drop-dead time period can be provided and can be greater than the pre-determined time period. For example, a drop-dead time period can include 24 hours, while the pre-determined time period includes 23 hours. In some examples, the drop-dead time period can be a time period that, if exceeded, provides an adverse results (e.g., non-reimbursement for the cost of the underlying ECG). In some examples, the pre-determined time period provides an indication of how close time-sensitive, patient-associated tasks are to reaching the drop-dead time period.

In the example of FIG. 9, the patient icons 930 each include patient information and patient data. The example patient information can include patient name, the patient gender, an identifier associated with the patient, an ECG summary, and/or patient date of birth (DOB). It is appreciated that implementations of the present disclosure can include additional and/or other patient data/information in a patient icon. In some examples, the patient data/information provided in the patient icons 930 can include recorded patient data/information. In some examples, the patient data/information provided in the patient icons 930 can include real-time patient data/information. For example, a patient icon 930 can be representative of a patient that is currently being monitored by one or more patient monitoring devices (e.g., as depicted in FIGS. 1 and 2), and the patient data displayed in the patient icon 930 can be updated in real-time based on data provided from the monitoring device(s).

In the depicted example, the icon groups are associated with locations and/or departments of the particular facility. For example, the icon group 922 is associated with the intensive care unit (ICU) of the facility, and the icon group 924 is associated with the "East Wing" of the facility. In some examples, icon groups can be associated with times before pre-determined time periods and/or drop-dead time periods are exceeded. For example, a first icon group can be associated with "1 hour" before a pre-determined time period or a drop-dead time period will be exceeded, and a second icon group can be associated with "12 hours" before the pre-determined time period or the drop-dead time period will be exceeded. In this manner, more urgent time-sensitive, patient-associated tasks can be separated from or highlighted relative to less urgent time-sensitive, patient-associated tasks.

In accordance with implementations of the present disclosure, the user can select a patient icon 930 from the screen 900 to initiate execution of a respective time-sensitive, patient associated task. In the example context, in response to user selection of a patient icon 930, an ECG screen associated with a respective patient is displayed.

FIG. 10 depicts an example ECG screen 1000 graphically representing an ECG on the display of a mobile device. In some examples, the ECG screen is displayed in response to user selection of a patient icon (e.g., a patient icon 930) from a "Time-Sensitive Tasks" screen (e.g., a "Time-Sensitive Tasks" screen 900). The example ECG discussed herein corresponds to a 12-lead ECG Implementations of the present disclosure are applicable to any appropriate type of ECG The ECG screen 1000 provides graphical information relating to the data collected from a patient monitoring device. In particular, the ECG screen 1000 provides cardiology information relating to data collected from an ECG monitoring device coupled to a patient.

The ECG screen 1000 includes a display region 1002 and a display region 1004. In the depicted example, the display region 1002 provides a grid of ECG trace windows 1010a-1010l (e.g., 4 columns by 3 rows, the first column including the leads I, II and III, the second column including the leads aVR, aVL and aVF, and the last two columns including the leads $V_1$-$V_6$). Each trace window 1010a-1010l includes a respective voltage trace 1005a-1005l corresponding to the respective lead over a period of time. In some examples, the trace windows 1010a-1010l can be used to zoom in and out of and to scroll along segments of the respective voltage traces 1005a-1005l.

The display region 1004 includes expanded trace windows, each expanded trace window corresponding to a trace window provided in the display region 1002. In the example of FIG. 10, expanded trace windows 1012a, 1012b are displayed and correspond to the trace windows 1010a, 1010b, respectively, of the display region 1002. In some examples, the expanded traced windows can be scrolled upward/downward within the display region 1004 to reveal additional expanded trace windows. For example, un-displayed expanded trace windows (e.g., expanded trace windows 1012c-1012l), or partially displayed, expanded trace windows (e.g., expanded trace window 1012b) can be scrolled into full view, while displayed trace windows (e.g., expanded trace windows 1012a, 1012b) can be scrolled from view.

The display region 1004 can display expanded trace windows 1012a-1012l having respective voltage traces 1013a-1013l, each voltage trace 1013a-1013l corresponding to voltage traces 1005a-1005l. The voltage traces 1013a-1013l are each provided as full traces for a particular period of time, graphically representing the ECG data collected over the particular period of time. In some examples, the user defines a desired time period for viewing ECG data by zooming in/out of and/or scrolling along one of the voltage traces 1005a-1005l to display a desired segment of the voltage traces 1005a-1005l within the trace windows 1010a-1010l. Accordingly, the trace display windows 1010a-1010l respectively display segments of the voltage traces 1005a-1005l, the segments corresponding to respective segments of the voltage traces 1013a-1013l displayed in the expanded trace windows 1012a-1012l. That is, each trace window 1010a-1010l can display a full trace or zoomed-in voltage trace 1005a-1005l corresponding to a voltage trace 1013a-1013l. In some examples, the voltage traces 1005a-1005l are synchronized with each other, such that scrolling and/or zooming of a voltage trace 1005a-1005l in one trace window 1010a-1010l results in an equivalent scrolling and/or zooming in each of the other trace windows 1010a-1010l. Consequently, each trace window 1010a-1010l displays its respective voltage trace 1005a-1005l for the same time period.

With continued reference to FIG. 10, a beveled scrubber bar 1020 can be provided in each of the trace windows 1012a-1012l. The beveled scrubber bar 1020 provides a viewing area 1022 having a width w. The viewing area 1022 displays a portion of the voltage trace 1013a-1013l corresponding to the portion of the voltage trace 1005a-1005l displayed in trace display windows 1010a-1010l. Accordingly, the width w generally corresponds to the time period of the voltage traces 1005a-1005l. In the example of FIG. 10, the width w corresponds to the time period between time t3 and t4. The beveled scrubber bars 1020 provide a graphical indicator that enables a user to quickly discern which portion of the voltage traces 1013a-1013l correspond to the voltage traces 1005a-1005l.

Further details of example ECG displays are provided in International App. No. PCT/US2012/021677, which claims the benefit of U.S. Prov. App. No. 61/433,824, the disclosures of which are expressly incorporated herein by reference in their entireties.

In accordance with implementations of the present disclosure, the screen 1000 includes an edit icon 1040. In some examples, user input to the edit icon 1040 (e.g., tap on) induces display of one or more option icons. In some examples, a drop-down menu is displayed, the drop-down menu including the one or more option icons. In some examples, the user is able to add a diagnosis, edit a diagnosis, delete a diagnosis and confirm a diagnosis. In some examples, the user can review the ECG in the screen 1000 and can select the edit icon 1040 to add, edit and/or delete a diagnosis. In some examples, the user can select the edit icon to confirm a diagnosis. For example, the user can select the edit icon 1040 to display the drop-down menu, the drop-down menu including a confirm icon. The user can select the confirm icon to confirm a diagnosis associated with the particular ECG In some examples, a confirmation signal associated with the particular ECG can be transmitted to the back-end system in response to selection of the confirm icon. In some examples, once the ECG has been confirmed, the patient-associated task (e.g., ECG consult) is determined to be completed.

Figure 11:
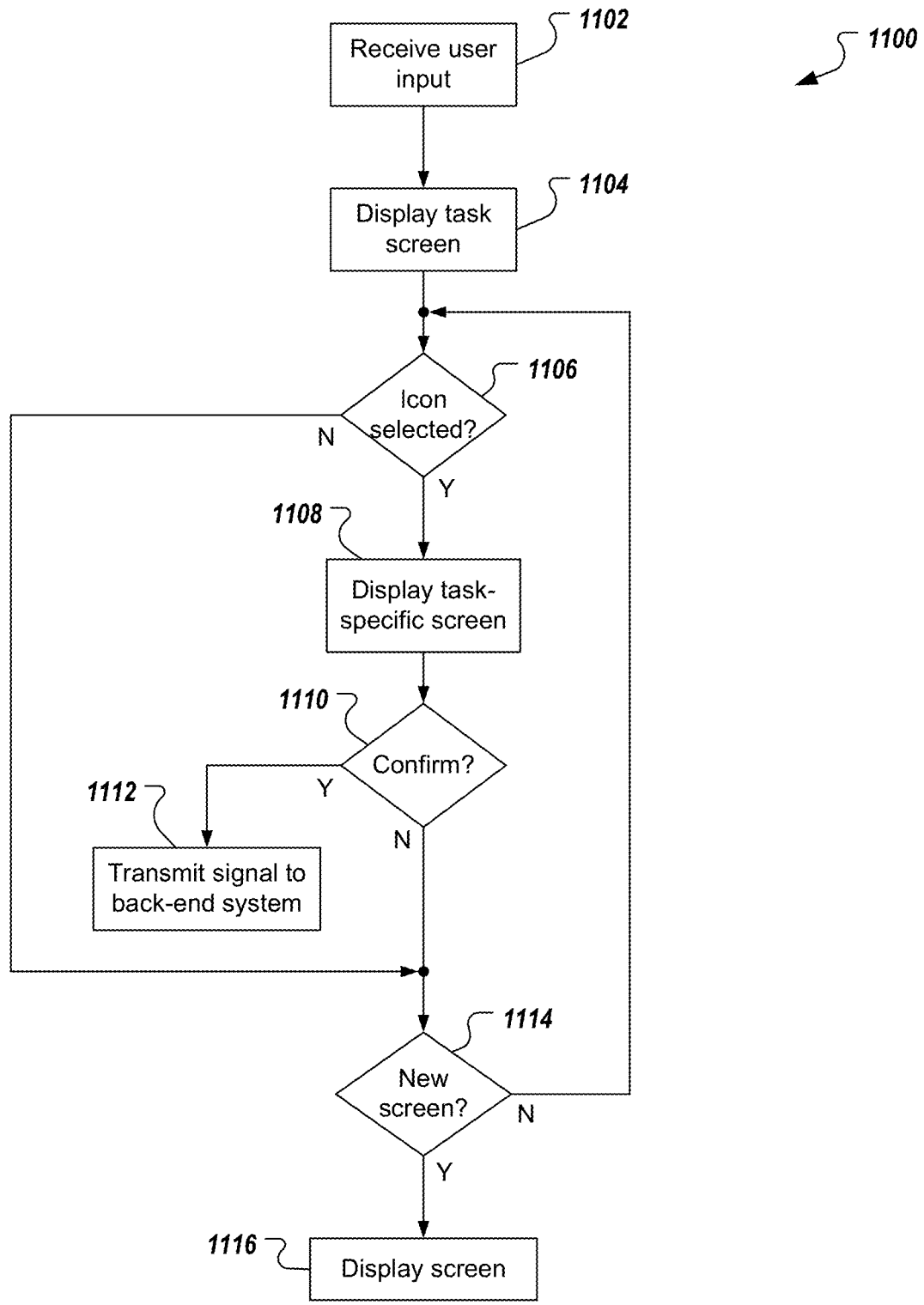
FIG. 11 is a flowchart illustrating an example process that can be executed in accordance with implementations of the present disclosure.

FIG. 11 depicts an example process 1100 that can be executed in accordance with implementations of the present disclosure. In some examples, the example process 1100 can be provided in one or more computer-executable programs that can be executed using one or more computing devices (e.g., the mobile device 102 and/or the DMS 160, 160').

User input is received (1102) and a task screen is displayed (1104). In some examples, the task screen is a "Time-Sensitive Tasks" screen that provides one or more patient icons that represent a time-sensitive, patient-associated task (e.g., the screen 900 of FIG. 9). It is determined whether an icon is selected (1104). For example, it is determined whether a patient icon representative of a time-sensitive, patient-associated task is selected. If an icon is not selected, it is determined whether a new screen is to be displayed (1114). For example, the user can choose to navigate to a different screen from the task-specific screen. If it is determined that a new screen is to be displayed, the new screen is displayed (1116). If it is determined that a new screen is not to be displayed, the example process 1100 loops back.

If an icon is selected, a task-specific screen is displayed (1108). In some examples, a task-specific screen displays patient data/information associated with the underlying time-sensitive task and enables the user to complete the task (e.g., the screen 1000 of FIG. 10). It is determined whether completion of the task is confirmed (1110). For example, the user can select a confirm option from the task-specific screen. If completion of the task is confirmed, a signal is transmitted to a back-end system (1112). In this manner, a back-end system managing the underlying task can be informed that the task has been attended to. If completion of the task is not confirmed, it is determined whether a new screen is to be displayed (1114). For example, the user can choose to navigate to a different screen from the task-specific screen. If it is determined that a new screen is to be displayed, the new screen is displayed (1116). If it is determined that a new screen is not to be displayed, the example process 1100 loops back.

Implementations of the present disclosure can be provided using digital electronic circuitry, or in computer hardware, firmware, software, or in combinations thereof. In some examples, implementations can be provided one or more computer program products, e.g., a computer program tangibly embodied in a machine-readable storage device, for execution by, or to control the operation of, data processing apparatus, and/or a programmable processor, a computer, or multiple computers. A computer program can be written in any form of programming language, including compiled or interpreted languages, and it can be deployed in any form, including as a stand-alone program or as a module, component, subroutine, or other unit suitable for use in a computing environment. A computer program can be deployed to be executed on one computer or on multiple computers at one site or distributed across multiple sites and interconnected by a communication network. Such a computer program can include modules and/or code segments for executing one or more of the features, aspects and/or implementations provided herein.

Operations in accordance with implementations of the present disclosure can be performed by one or more programmable processors executing a computer program product to perform functions by operating on input data and generating output. By way of example, a computer program product can include modules and/or code segments corresponding to each of the method steps, aspects and/or features provided herein. Method steps can also be performed by, and apparatus of the present disclosure can be implemented as, special purpose logic circuitry, e.g., an FPGA (field programmable gate array) or an ASIC (application-specific integrated circuit).

Processors suitable for the execution of a computer program include, by way of example, both general and special purpose microprocessors, and any one or more processors of any kind of digital computer. Generally, a processor will receive instructions and data from a read-only memory or a random access memory or both. Elements of a computer can include a processor for executing instructions and one or more memory devices for storing instructions and data. Generally, a computer can also include, or be operatively coupled to receive data from or transfer data to, or both, one or more mass storage devices for storing data, e.g., magnetic, magneto-optical disks, or optical disks. Information carriers suitable for embodying computer program instructions and data include all forms of non-volatile memory, including by way of example semiconductor memory devices, e.g., EPROM, EEPROM, and flash memory devices; magnetic disks such as internal hard disks and removable disks; magneto-optical disks; and CD-ROM and DVD-ROM disks. The processor and the memory can be supplemented by, or incorporated in special purpose logic circuitry.

The present disclosure can be implemented in a system including, but not limited to the example systems described herein, which include a back-end component, e.g., as a data server, or that includes a middleware component, e.g., an application server, or that includes a front-end component, e.g., a client device, such as the mobile device 102, having a graphical user interface or a Web browser through which a user can interact with an implementation of the invention, or any combination of such back-end, middleware, or front-end components. The components of the system can be interconnected by any form or medium of digital data communication, e.g., a communication network.

A number of implementations have been described. Nevertheless, it will be understood that various modifications may be made without departing from the spirit and scope of the disclosure. For example, steps of the present disclosure can be performed in a different order and still achieve desirable results. Accordingly, other implementations are within the scope of the following claims.

The invention claimed is:

1. A method for providing a user of a mobile device access to patient information and patient physiological data, the method comprising:
   receiving, by one or more processors, user input indicating a user command to display a task screen;
   in response to the user input, processing, by the one or more processors, user-specific data to determine one or more patient icons, each patient icon representing a time-sensitive, patient-associated task;
   displaying the task screen on the mobile device, the task screen displaying one or more patient icon groups, each patient icon group comprising a patient icon of the one or more patient icons;
   receiving, by the one or more processor, a user selection of a patient icon from the one or more patient icon groups; and
   in response to the user selection of the patient icon, displaying a plurality of windows on the mobile device, the plurality of windows comprising:
      a first window displaying first health information associated with a period of time, the first health information being a part of the patient physiological data and comprising electrocardiogram (ECG) data, wherein the first window comprises an indicator that indicates a sub-period of time with respect to the period of time, and
      a second window associated with the first window and displaying second health information associated with the sub-period of time that is a portion of the period of time associated with the first window.

2. The method of claim 1, wherein the time-sensitive, patient-associated task of each patient icon comprises a pending task.

3. The method of claim 1, further comprising, in response to user selection of a patient icon, displaying a task-specific screen, the task-specific screen comprising patient data and/or patient information associated with an underlying task.

4. The method of claim 1, further comprising receiving user input indicating completion of the time-sensitive, patient-associated task of the patient icon, and in response, providing a signal to a back-end system indicating completion of the time-sensitive, patient-associated task.

5. The method of claim 1, further comprising removing the patient icon from display in the task screen.

6. The method of claim 1, wherein each time-sensitive, patient-associated task is determined to be within a threshold time period.

7. The method of claim 6, wherein the time-sensitive, patient-associated task is determined to be within the threshold time period when a difference between a current time and a time associated with the time-sensitive, patient-associated task is within the threshold time period.

8. A computer-readable storage device coupled to one or more processors and having instructions stored thereon which, when executed by the one or more processors, cause the one or more processors to perform operations for providing a user of a mobile device access to patient information and patient physiological data, the operations comprising:
   receiving, by the one or more processors, user input indicating a user command to display a task screen;
   in response to the user input, processing, by the one or more processors, user-specific data to determine one or more patient icons, each patient icon representing a time-sensitive, patient-associated task;
   displaying the task screen on the mobile device, the task screen displaying one or more patient icon groups, each patient icon group comprising a patient icon of the one or more patient icons;
   receiving, by the one or more processor, a user selection of a patient icon from the one or more patient icon groups; and
   in response to the user selection of the patient icon, displaying a plurality of windows on the mobile device, the plurality of windows comprising:
      a first window displaying first health information associated with a period of time, the first health information being a part of the patient physiological data and comprising electrocardiogram (ECG) data, wherein the first window comprises an indicator that indicates a sub-period of time with respect to the period of time, and
      a second window associated with the first window and displaying second health information associated with the sub-period of time that is a portion of the period of time associated with the first window.

9. A system, comprising:
   one or more processors; and
   a computer-readable storage medium in communication with the one or more processors and having instructions stored thereon which, when executed by the one or more processors, cause the one or more processors to perform operations for providing a user of a mobile device access to patient information and patient physiological data, the operations comprising:
      receiving, by the one or more processors, user input indicating a user command to display a task screen;
      in response to the user input, processing, by the one or more processors, user-specific data to determine one or more patient icons, each patient icon representing a time-sensitive, patient-associated task;
      displaying the task screen on the mobile device, the task screen displaying one or more patient icon groups, each patient icon group comprising a patient icon of the one or more patient icons;
      receiving, by the one or more processor, a user selection of a patient icon from the one or more patient icon groups; and in response to the user selection of the patient icon, displaying a plurality of windows on the mobile device, the plurality of windows comprising:
- a first window displaying first health information associated with a period of time, the first health information being a part of the patient physiological data and comprising electrocardiogram (ECG) data, wherein the first window comprises an indicator that indicates a sub-period of time with respect to the period of time, and
- a second window associated with the first window and displaying second health information associated with the sub-period of time that is a portion of the period of time associated with the first window.

* * * * *